United States Patent
Diamond

(10) Patent No.: US 10,596,254 B2
(45) Date of Patent: Mar. 24, 2020

(54) SYNTHETIC CONJUGATE OF CPG DNA AND T-HELP/CTL PEPTIDE

(71) Applicant: CITY OF HOPE, Duarte, CA (US)

(72) Inventor: Don J. Diamond, Glendora, CA (US)

(73) Assignee: City of Hope, Duarte, CA (US)

( * ) Notice: Subject to any disclaimer, the term of this patent is extended or adjusted under 35 U.S.C. 154(b) by 23 days.

(21) Appl. No.: 15/963,173

(22) Filed: Apr. 26, 2018

(65) Prior Publication Data

US 2018/0243409 A1 Aug. 30, 2018

Related U.S. Application Data

(60) Continuation of application No. 14/736,897, filed on Jun. 11, 2015, now Pat. No. 9,974,854, which is a division of application No. 11/008,958, filed on Dec. 13, 2004, now Pat. No. 9,090,673.

(60) Provisional application No. 60/528,706, filed on Dec. 12, 2003.

(51) Int. Cl.
| | |
|---|---|
| *A61K 39/39* | (2006.01) |
| *C07K 14/005* | (2006.01) |
| *C12N 7/00* | (2006.01) |
| *A61K 39/385* | (2006.01) |
| *A61K 39/21* | (2006.01) |
| *A61K 39/00* | (2006.01) |

(52) U.S. Cl.
CPC .............. *A61K 39/39* (2013.01); *A61K 39/21* (2013.01); *A61K 39/385* (2013.01); *C07K 14/005* (2013.01); *C12N 7/00* (2013.01); *A61K 2039/55516* (2013.01); *A61K 2039/55561* (2013.01); *A61K 2039/605* (2013.01); *A61K 2039/6025* (2013.01); *C07K 2319/00* (2013.01); *C12N 2740/16022* (2013.01); *C12N 2740/16034* (2013.01); *C12N 2740/16122* (2013.01)

(58) Field of Classification Search
None
See application file for complete search history.

(56) References Cited

U.S. PATENT DOCUMENTS

| | | | |
|---|---|---|---|
| 5,314,813 A | 5/1994 | Peterson et al. | |
| 5,529,921 A | 6/1996 | Peterson et al. | |
| 5,736,142 A | 4/1998 | Sette et al. | |
| 5,747,269 A | 5/1998 | Rammensee et al. | |
| 5,827,737 A | 10/1998 | Peterson et al. | |
| 5,981,706 A * | 11/1999 | Wallen | C07K 14/39 210/656 |
| 6,001,365 A * | 12/1999 | Peterson | A61K 38/1774 424/193.1 |
| 6,011,146 A | 1/2000 | Mottez et al. | |
| 6,207,646 B1 | 3/2001 | Krieg et al. | |
| 6,218,371 B1 | 4/2001 | Krieg et al. | |
| 6,248,564 B1 * | 6/2001 | Walter | C07K 14/70539 424/178.1 |
| 6,268,411 B1 | 7/2001 | Schneck et al. | |
| 6,406,705 B1 | 6/2002 | Davis et al. | |
| 6,413,935 B1 | 7/2002 | Sette et al. | |
| 6,472,375 B1 | 10/2002 | Hoon et al. | |
| 6,514,948 B1 | 2/2003 | Raz et al. | |
| 6,544,521 B2 * | 4/2003 | Diamond | A61K 39/25 424/186.1 |
| 6,558,670 B1 | 5/2003 | Friede et al. | |
| 6,562,345 B1 | 5/2003 | Diamond | |
| 6,602,510 B1 | 8/2003 | Fikes et al. | |
| 6,632,435 B1 | 10/2003 | Diamond | |
| 6,673,556 B2 | 1/2004 | Nixon et al. | |
| 6,726,910 B2 * | 4/2004 | Diamond | A61K 39/245 424/186.1 |
| 6,734,013 B2 | 5/2004 | Schneck et al. | |
| 6,843,992 B2 | 1/2005 | Diamond | |
| 6,951,651 B2 * | 10/2005 | Diamond | A61K 39/245 424/184.1 |
| 6,974,574 B2 * | 12/2005 | Walker | C07K 14/005 424/185.1 |
| 6,977,074 B2 | 12/2005 | Kündig et al. | |
| 7,160,685 B2 | 1/2007 | Diamond | |
| 7,537,767 B2 * | 5/2009 | Bachmann | A61K 39/39 424/185.1 |
| 8,008,267 B2 | 8/2011 | Kandimalla et al. | |
| 8,088,388 B2 | 1/2012 | Sokoll | |
| 8,263,091 B2 | 9/2012 | Klinman et al. | |
| 8,580,276 B2 | 11/2013 | Diamond et al. | |
| 8,946,175 B1 | 2/2015 | Kandimalla et al. | |
| 9,090,673 B2 * | 7/2015 | Diamond | A61K 39/385 |
| 9,453,227 B2 | 9/2016 | Diamond et al. | |
| 9,974,854 B2 * | 5/2018 | Diamond | A61K 39/385 |
| 10,023,657 B2 * | 7/2018 | Luescher | A61K 39/385 |
| 10,030,065 B2 * | 7/2018 | Brix | B82Y 5/00 |
| 10,138,271 B2 * | 11/2018 | Schlom | A61K 39/0011 |
| 2001/0036461 A1 | 11/2001 | Haynes et al. | |
| 2002/0119149 A1 | 8/2002 | Jakobsen et al. | |
| 2002/0142389 A1 | 10/2002 | Jakobsen et al. | |
| 2002/0146746 A1 | 10/2002 | Nixon et al. | |
| 2002/0164721 A1 | 11/2002 | Firat et al. | |
| 2002/0164751 A1 | 11/2002 | Short et al. | |

(Continued)

FOREIGN PATENT DOCUMENTS

| | | |
|---|---|---|
| WO | 9741440 A1 | 11/1997 |
| WO | WO-9741440 A1 * 11/1997 | ....... G01N 33/56977 |

(Continued)

OTHER PUBLICATIONS

Daftarian et al, Vaccine, 2005, 23:3453-3468. available online: Feb. 12, 2005 (Year: 2005).*

(Continued)

*Primary Examiner* — Nita M. Minnifield
(74) *Attorney, Agent, or Firm* — Rothwell, Figg, Ernst & Manbeck, P.C.

(57) ABSTRACT

Highly effective vaccine compositions are constructed according to the methods of this invention. The methods are amenable to use with any peptidic antigen sequence and involve covalent attachment of an immunostimulatory nucleotide sequence to an antigenic peptide sequence. Preferred antigenic peptides are fusion peptides made up of one or more CTL epitope peptides in sequence fused to a T helper peptide.

8 Claims, 22 Drawing Sheets

Specification includes a Sequence Listing.

(56) References Cited

U.S. PATENT DOCUMENTS

| | | | |
|---|---|---|---|
| 2003/0022820 A1 | 1/2003 | Sherman | |
| 2003/0077318 A1 | 4/2003 | Cai et al. | |
| 2003/0091599 A1 | 5/2003 | Davis et al. | |
| 2003/0096314 A1* | 5/2003 | Steinman | C12N 5/0639 435/7.2 |
| 2003/0099663 A1 | 5/2003 | Fleitmann et al. | |
| 2003/0118602 A1 | 6/2003 | Diamond | |
| 2003/0124718 A1* | 7/2003 | Fuller | C07K 14/005 435/320.1 |
| 2003/0152580 A1 | 8/2003 | Sette et al. | |
| 2003/0165478 A1* | 9/2003 | Sokoll | A61K 39/0006 424/93.21 |
| 2003/0224980 A1 | 12/2003 | Diamond | |
| 2004/0101534 A1* | 5/2004 | Diamond | A61K 39/245 424/186.1 |
| 2004/0223977 A1* | 11/2004 | Diamond | A61K 39/21 424/188.1 |
| 2005/0158336 A1* | 7/2005 | Diamond | A61K 39/385 424/192.1 |
| 2005/0175627 A1* | 8/2005 | Schneider | A61K 39/21 424/188.1 |
| 2006/0251623 A1* | 11/2006 | Bachmann | A61K 39/00 424/93.2 |
| 2007/0026015 A1* | 2/2007 | Braun | A61K 39/00 424/208.1 |
| 2007/0248584 A1 | 10/2007 | Kent | |
| 2010/0316667 A1 | 12/2010 | Diamond et al. | |
| 2011/0097417 A1* | 4/2011 | Bachmann | A61K 39/39 424/499 |
| 2013/0028923 A1 | 1/2013 | Tahara et al. | |
| 2016/0000906 A1* | 1/2016 | Diamond | A61K 39/385 424/188.1 |
| 2017/0072071 A1 | 3/2017 | Gros | |
| 2018/0243409 A1* | 8/2018 | Diamond | A61K 39/385 |
| 2019/0022212 A1* | 1/2019 | Barouch | A61P 31/18 |
| 2019/0031759 A1* | 1/2019 | Reiter | C07K 16/2833 |
| 2019/0055289 A1* | 2/2019 | Brander | A61K 39/21 |
| 2019/0055290 A1* | 2/2019 | Barouch | C07K 14/005 |
| 2019/0062389 A1* | 2/2019 | Miyakawa | A61K 38/00 |
| 2019/0085048 A1* | 3/2019 | Brix | B82Y 5/00 |

FOREIGN PATENT DOCUMENTS

| | | | | |
|---|---|---|---|---|
| WO | 9816247 A1 | 4/1998 | | |
| WO | 9821233 A2 | 5/1998 | | |
| WO | WO-9850423 A2 * | 11/1998 | | A61K 39/0005 |
| WO | WO-9902183 A2 * | 1/1999 | | A61K 39/0011 |
| WO | WO-9911775 A1 * | 3/1999 | | C07K 14/70539 |
| WO | WO-9929182 A1 * | 6/1999 | | C07K 14/4702 |
| WO | WO-9945954 A1 * | 9/1999 | | C07K 14/36 |
| WO | WO-9958658 A2 * | 11/1999 | | A61K 39/385 |
| WO | 03015711 A2 | 2/2003 | | |
| WO | WO-2004000873 A2 * | 12/2003 | | A61K 39/245 |
| WO | 2004056391 A1 | 7/2004 | | |
| WO | WO-2004085466 A2 * | 10/2004 | | A61K 39/21 |
| WO | WO-2004085635 A1 * | 10/2004 | | A61K 39/0011 |
| WO | WO-2005004907 A1 * | 1/2005 | | A61K 39/00 |
| WO | WO-2005030964 A1 * | 4/2005 | | A61K 39/21 |
| WO | WO-2005035779 A2 * | 4/2005 | | A61K 39/00 |

OTHER PUBLICATIONS

BenMohamed et al, Human Immunology, 2000, 61:764-779. (Year: 2000).*
BenMohamed et al, Immunology, 2002, 106:113-121. (Year: 2002).*
Daftarian et al, Journal Immunology, 2003, 171:4028-4039. (Year: 2003).*
Domingo et al, Vaccine, 2003, 21:1502-1509 (Year: 2003).*
Ahlers et al., "High-Affinity T Helper Epitope Induces Complementary Helper and APC Polarization, Increased CTL, and Protection Against Viral Infection," J. Clin. Invest., 108(11)1677-85, 2001.
Alexander et al., "Development of High Potency Universal DR-Restricted Helper Epitopes by Modification of High Affinity DR-Blocking Peptides," Immunity 1:751-761, 1994.
Alexander et al., "A Decaepitope Polypeptide Primes for Multiple CD8+ INF-γ and Th Lymphocyte Responses: Evaluation of Multiepitope Polypeptides as a Mode for Vaccine Delivery," J. Immunol., 168:6189-6198, 2002.
Benmohamed et al., "Induction of CTL Response by a Minimal Epitope Vaccine in HLA A*0201/DR1 Transgenic Mice: Dependence on HLA Class II Restricted $T_H$ Response," Hum. Immunol., 61:764-779, 2000.
Cafaro et al., "Vaccination with DNA Containing tat Coding Sequences and Unmethylated CpG Motifs Protects Cynomolgus Monkeys Upon Infection with Simian/Human Immunodeficiency Virus (SHIV89.6P)," Vaccine, 19:2862-2877, 2001.
Chee et al., "Analysis of the Protein-Coding Content of the Sequence of Human cytomegalovirus Strain AD169," Curr. Topics Microbiol. Immunol., 154:126-169, 1990.
Cho et al., "Immunostimulatory DNA-based Vaccines Induce Cytotoxic Lymphocyte Activity by a T-Helper Cell-Independent Mechanism," Nat. Biotechnol., 18:509-514, 2000.
Cho et al., "IFN-αβ Promote Priming of Antigen-Specific CD8+ and CD4+ T Lymphocytes by Immunostimulatory DNA-Based Vaccines," J. Immunol., 168:4907-4913, 2002.
Chu et al., "CpG Oligodeoxynucleotides Act as Adjuvants that Switch on T Helper 1 (Th1) Immunity," J. Exp. Med. 186(10):1623-1631, 1997.
Del Val et al., "Protection Against Lethal Cytomegalovirus Infection by a Recombinant Vaccine Containing a Single Nonameric T-Cell Epitope," J. Virol., 65(7):3641-3646, 1991.
Diamond et al., "Development of a Candidate HLA A*0201 Restricted Peptide Based Vaccine Against HCMV Infection," Blood 90(5):1751-1767, 1997.
Elias et al., "Strong Cytosine-Guanosine-Independent Immunostimulation in Humans and other Primates by Synthetic Oligodeoxynucleotides with PyNTTTTGT Motifs," J. Immunol., 171:3697-3704, 2003.
Freytag et al., "Bacterial Toxins as Mucosal Adjuvants," Curr. Topics Microbiol. Immunol., 236:215-236, 1999.
Gürsel et al., "Differential and Competitive Activation of Human Immune Cells by Distinct Classes of CpG Oligodeoxynucleotide," J. Leukocyte Biol., 71:813-820, 2002.
Ho et al., "An Immunomodulatory GpG Oligonucleotide for the Treatment of Autoimmunity via the Innate and Adaptive Immune Systems," J. Immunol., 171:4920-4926, 2003.
Horner et al., "Immunostimulatory DNA-Based Vaccines Elicit Multifaceted Immune Responses Against HIV at Systemic and Mucosal Sites," J. Immunol., 167:1584-1591, 2001.
Ishioka et al. "Utilization of MHC Class I Transgenic Mice for Development of Minigen DNA Vaccines Encoding Multiple HLA-Restricted CTL Epitopes," J. Immunol., 162:3915-3925, 1999.
Klinman et al., "CpG DNA Augments the Immunogenicity of Plasmid DNA Vaccines," Curr. Topics Microbiol. Immunol. 247:131-142, 2000.
Klinman et al., "CpG DNA: Recognition by and Activation of Monocytes," Microbes and Infection 4:897-901, 2002.
Krieg et al., "CpG Motifs in Bacterial DNA and Their Immune Effects," Annu. Rev. Immunol. 20:709-760, 2002.
Krieg et al., "CpG Motifs in Bacterial DNA Trigger Direct B-Cell Activation," Nature 374:546-549, Apr. 1995.
Krieg et al., "Enhancing Vaccines with Immune Stimulatory CpG DNA," Current Opinion Mol. Ther., 3(1):15-24, 2001.
Krieg et al., "Sequence Motifs in Adenoviral DNA Block Immune Activation by Stimulatory CpG Motifs," Proc. Natl. Acad. Sci. USA, 95:12631-12636, 1998.
Krug et al., "Identification of CpG Oligonucleotide Sequences with High Induction of IFN-α/β in Plasmacytoid Dendritic Cells," Eur. J. Immunol., 31:2154-2163, 2001.
Lipford et al., "CpG-Containing Synthetic Oligonucleotides Promote B and Cytotoxic T Cell Responses to Protein Antigen: A New Class of Vaccine Adjuvants," Eur. J. Immunol. 27:2340-44, 1997.

(56) References Cited

OTHER PUBLICATIONS

Meseda et al., "Prime-Boost Immunization with DNA and Modified Vaccinia Virus Ankara Vectors Expressing Herpes Simplex Virus-2 Glycoprotein D Elicits Greater Specific Antibody and Cytokine Responses than DNA Vaccine Alone," J. Infect. Dis., 186:1065-73, 2002.
Millan et al., "CpG DNA Can Induce Strong Th1 Humoral and Cell-Mediated Immune Response Against Hepatitis B Surface Antigen in Young Mice," Proc. Natl. Acad. Sci. USA, 95:15553-15558, 1998.
Moldoveanu et al., "CpG DNA, a Novel Immune Enhancer for Systemic and Mucosal Immunization with Influenza Virus," Vaccine, 16(11/12):1216-1224, 1998.
Oseroff et al., "Pools of Lipidated HTL-CTL Constructs Prime for Multiple HBV and HCV CTL Epitope Responses," Vaccine, 16(8):823-833, 1998.
Pande et al., "Human Cytomegalovirus Strain Towne pp65 Gene: Nucleotide Sequence and Expression in *Escherichia coli*," Virology 182: 220-228, 1991.
Sano et al., "Oligodeoxynucleotides Without CpG Motifs Work as Adjuvant for the Induction of Th2 Differentiation in a Sequence-Independent Manner," J. Immunol., 170:2367-2373, 2003.
Schirmbeck et al., "Antigenic Epitopes Fused to Cationic Peptide Bound to Oligonucleotides Facilitate Toll-Like Receptor 9-Dependent, but CD4+ T Cell Help-Independent, Priming of CD8+ T Cells," J. Immunol., 171:5198-5207, 2003.
Shirai et al., "Helper-Cytotoxic T Lymphocyte (CTL) Determinant Linkage Required for Priming of Anti-HIV CD8+ CTL in Vivo with Peptide Vaccine Constructs," J. Immunol., 152:549-556, 1994.
Tighe et al., "Conjugation of Immunostimulatory DNA to the Short Ragweed Allergen Amb a 1 Enhances its Immunogenicity and Reduces its Allergenicity," J. Allergy Clin. Immunol., 106(1, pt.1): 124-134, 2000.
Tighe et al., "Conjugation of Protein to Immunostimulatory DNA Results in a Rapid, Long-lasting and Potent Induction of Cell-Mediated and Humoral Immunity," Eur. J. Immunol., 30:1939-1947, 2000.
Verthelyi et al., "Human Peripheral Blood Cells Differentially Recognize and Respond to Two Distinct CpG Motifs," J. Immunol., 166:2372-2377, 2001.
Zaia et al., "Status of Cytomegalovirus Prevention and Treatment in 2000," Am. Soc. Hematology, pp. 339-355, 2000.
Daftarian et al., "Immunization with Th-CTL Fusion Peptide and Cytosine-phosphate-quanine DNA in Transgenic HLA-A2 Mice Includes Recognition of HIV-Infected T Cells and Clears Vaccinia Virus Challenge," The Journal of Immunology, Oct. 15, 2003, vol. 171, pp. 4028-4039.
Tighe et al., "Conjugation of Protein to Immunostimulatory DNA Results in a Rapid, Long-Lasting and Potent Induction of Cell-Mediated and Humoral Immunity," European Journal of Immunology, 2000, vol. 30, pp. 1939-1947.
La Rosa et al., "Preclinical Development of an Adjuvant-Free Peptide Vaccine with Activity Against CMV pp65 in HLA Transgenic Mice," Blood, Nov. 15, 2002, vol. 100, pp. 3681-3689.
U.S. Appl. No. 60/444,175, filed Feb. 3, 2003, pp. 1-26.
Diamond et al, Blood, Nov. 16, 2004, vol. 104, No. 11, Part 2, pp. 51B (Abstract Only).
Davila et al, Cancer Research, Jun. 15, 2003, 63:3281-3288.
Daftarian et al, Vaccine 23 (2005) 3453-3468.

* cited by examiner

SEQUENCE LISTING

```
<160> NUMBER OF SEQ ID NOS: 12

<210> SEQ ID NO 1
<211> LENGTH: 22
<212> TYPE: PRT
<213> ORGANISM: Artificial Sequence
<220> FEATURE:
<223> OTHER INFORMATION: fusion peptide with HIV and synthetic
      components
<220> FEATURE:
<221> NAME/KEY: MISC_FEATURE
<222> LOCATION: (1)..(22)
<223> OTHER INFORMATION: X is cyclohexylalanine

<400> SEQUENCE: 1

Ala Lys Xaa Val Ala Ala Trp Thr Leu Lys Ala Ala Ala Ile Leu Lys
1               5                   10                  15

Glu Pro Val His Gly Val
            20
```

-continued

```
<210> SEQ ID NO 2
<211> LENGTH: 25
<212> TYPE: PRT
<213> ORGANISM: Artificial Sequence
<220> FEATURE:
<223> OTHER INFORMATION: fusion peptide with HIV and synthetic
      components
<220> FEATURE:
<221> NAME/KEY: MISC_FEATURE
<222> LOCATION: (1)..(25)
<223> OTHER INFORMATION: X is cyclohexylalanine

<400> SEQUENCE: 2

Lys Ser Ser Ala Lys Xaa Val Ala Ala Trp Thr Leu Lys Ala Ala Ala
1               5                   10                  15

Ser Leu Tyr Asn Thr Val Ala Thr Leu
            20                  25

<210> SEQ ID NO 3
<211> LENGTH: 32
<212> TYPE: PRT
<213> ORGANISM: Artificial Sequence
<220> FEATURE:
<223> OTHER INFORMATION: fusion peptide with HIV and synthetic
      components
<220> FEATURE:
<221> NAME/KEY: MISC_FEATURE
<222> LOCATION: (1)..(32)
<223> OTHER INFORMATION: X is cyclohexylalanine

<400> SEQUENCE: 3

Ala Lys Xaa Val Ala Ala Trp Thr Leu Lys Ala Ala Ala Ile Leu Lys
1               5                   10                  15

Glu Pro Val His Gly Val Lys Ser Leu Tyr Asn Thr Val Ala Thr Leu
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: fusion peptide with HIV and synthetic
      components
<220> FEATURE:
<221> NAME/KEY: MISC_FEATURE
<222> LOCATION: (1)..(32)
<223> OTHER INFORMATION: X is cyclohexylalanine

<400> SEQUENCE: 4

Ala Lys Xaa Val Ala Ala Trp Thr Leu Lys Ala Ala Ala Ile Leu Lys
1               5                   10                  15

Glu Pro Val His Gly Val Asn Ser Leu Tyr Asn Thr Val Ala Thr Leu
            20                  25                  30

<210> SEQ ID NO 5
<211> LENGTH: 9
<212> TYPE: PRT
<213> ORGANISM: Human immunodeficiency virus

<400> SEQUENCE: 5

Ile Leu Lys Glu Pro Val His Gly Val
1               5

<210> SEQ ID NO 6
<211> LENGTH: 9
<212> TYPE: PRT
<213> ORGANISM: Human immunodeficiency virus
```

```
<400> SEQUENCE: 6

Ser Leu Tyr Asn Thr Val Ala Thr Leu
1               5

<210> SEQ ID NO 7
<211> LENGTH: 20
<212> TYPE: DNA
<213> ORGANISM: Artificial Sequence
<220> FEATURE:
<223> OTHER INFORMATION: immunostimulatory nucleotide sequence
<220> FEATURE:
<221> NAME/KEY: misc_feature
<222> LOCATION: (1)..(1)
<223> OTHER INFORMATION: modified to thiohexyl

<400> SEQUENCE: 7
tccatgacgt tcctgacgtt                                                  20

<210> SEQ ID NO 8
<211> LENGTH: 20
<212> TYPE: DNA
<213> ORGANISM: Artificial Sequence
<220> FEATURE:
<223> OTHER INFORMATION: immunostimulatory nucleotide sequence
<220> FEATURE:
<221> NAME/KEY: misc_feature
<222> LOCATION: (1)..(20)
<223> OTHER INFORMATION: fully phosphorothioated backbone
<220> FEATURE:
<221> NAME/KEY: misc_feature
<222> LOCATION: (1)..(1)
<223> OTHER INFORMATION: modified to thiohexyl

<400> SEQUENCE: 8
tccatgacgt tcctgacgtt                                                  20

<210> SEQ ID NO 9
<211> LENGTH: 20
<212> TYPE: DNA
<213> ORGANISM: Artificial Sequence
<220> FEATURE:
<223> OTHER INFORMATION: immunostimulatory nucleotide sequence
<220> FEATURE:
<221> NAME/KEY: misc_feature
<222> LOCATION: (1)..(20)
<223> OTHER INFORMATION: fully phosphorothioated backbone
<220> FEATURE:
<221> NAME/KEY: misc_feature
<222> LOCATION: (1)..(1)
<223> OTHER INFORMATION: modified to Amidite-A aldehyde linker

<400> SEQUENCE: 9
tccatgacgt tcctgacgtt                                                  20

<210> SEQ ID NO 10
<211> LENGTH: 24
<212> TYPE: DNA
<213> ORGANISM: Artificial Sequence
<220> FEATURE:
<223> OTHER INFORMATION: immunostimulatory nucleotide sequence
<220> FEATURE:
<221> NAME/KEY: misc_feature
<222> LOCATION: (1)..(24)
<223> OTHER INFORMATION: phosphorothioate-substituted

<400> SEQUENCE: 10
tcgtcgtttt gtcgttttgt cgtt                                             24
```

```
<210> SEQ ID NO 11
<211> LENGTH: 20
<212> TYPE: DNA
<213> ORGANISM: Artificial Sequence
<220> FEATURE:
<223> OTHER INFORMATION: immunostimulatory nucleotide sequence
<220> FEATURE:
<221> NAME/KEY: misc_feature
<222> LOCATION: (1)..(2)
<223> OTHER INFORMATION: phosphorothioate linkages
<220> FEATURE:
<221> NAME/KEY: misc_feature
<222> LOCATION: (3)..(14)
<223> OTHER INFORMATION: phosphodiester linkages
<220> FEATURE:
<221> NAME/KEY: misc_feature
<222> LOCATION: (15)..(19)
<223> OTHER INFORMATION: phosphorothioate linkages
<220> FEATURE:
<221> NAME/KEY: misc_feature
<222> LOCATION: (20)..(20)
<223> OTHER INFORMATION: phosphodiester linkages

<400> SEQUENCE: 11
gggggacgat cgtcggggggg                                              20

<210> SEQ ID NO 12
<211> LENGTH: 13
<212> TYPE: PRT
<213> ORGANISM: Artificial Sequence
<220> FEATURE:
<223> OTHER INFORMATION: synthetic promiscuous T helper peptide epitope
<220> FEATURE:
<221> NAME/KEY: MISC_FEATURE
<222> LOCATION: (1)..(13)
<223> OTHER INFORMATION: X is cyclohexylalanine

<400> SEQUENCE: 12

Ala Lys Xaa Val Ala Ala Trp Thr Leu Lys Ala Ala Ala
1               5                   10
```

SYNTHETIC CONJUGATE OF CPG DNA AND T-HELP/CTL PEPTIDE

CROSS-REFERENCE TO RELATED APPLICATIONS

This application is a continuation of U.S. patent application Ser. No. 14/736,897 filed on 11 Jun. 2015, which is a division of U.S. patent application Ser. No. 11/008,958 filed on 13 Dec. 2004, now U.S. Pat. No. 9,090,673, which in turn is related to and claims benefit of U.S. provisional patent application Ser. No. 60/528,706 filed on 12 Dec. 2003. Each application is hereby incorporated by reference in its entirety.

STATEMENT REGARDING FEDERALLY-SPONSORED RESEARCH

This invention was made with government support in the form of Grant No. AI44313 from the United States Department of Health and Human Services, National Institutes of Health, DAIDS and Grant No. PO1CA30206 from the United States Department of Health and Human Services, National Institutes of Health, NCI. The United States government has certain rights in the invention.

SUBMISSION OF SEQUENCE LISTING

The present application is being filed along with a Sequence Listing in electronic format. The Sequence Listing is entitled 1954578US2SequenceListing.txt, created on 29 Jan. 2018 and is 5 kb in size. The information in the electronic format of the Sequence Listing is incorporated herein by reference in their entirety.

BACKGROUND OF THE INVENTION

Technical Field

This invention relates to the field of immunology. In particular, the invention involves methods for presenting immunogenic substances to the body in a manner that results in enhanced recognition of the substance by the immune system. The compounds and methods of the invention consequently are useful for preparation of vaccines, methods of vaccinating and vaccination for both protection from and treatment for diseases such as bacterial and viral diseases or any disease amenable to prevention or treatment by vaccine, including cancer. Diseases previously resistant to attempts to vaccinate against them, such as HIV disease are of particular interest in uses for the invention.

Description of the Background Art

Long-term administration of anti-viral drugs is expensive and often involves unpleasant or even dangerous side effects. Increasing numbers of pathogenic bacteria are becoming drug-resistant. Treatment of infectious disease in the current health care environment therefore often is problematic. Moreover, prevention of disease, where possible, is far preferable to treatment. Therefore, non-toxic and effective vaccines against a variety of pathogens would be highly desirable. However, no vaccine, approved as safe and effective by the U.S. Food and Drug Administration, currently exists for a number of diseases, including HIV. Even where vaccines for a particular pathologic agent do exist, more potent, more effective and safer vaccines are needed in the art.

A vaccine that can stimulate CTL and a T-help cellular immune response can be used both as a prophylactic vaccine and also as part of a treatment for those who are infected. Stimulation of CTL is important in restricting viral replication during both the acute and chronic stages of infection; these CTL responses are critical in the immunological defense against such diseases as HIV, including resistance to infection in the first instance and long-term non-progression to AIDS in infected persons. T helper responses also are necessary for an optimal immune response to any infectious disease. A vaccine which effectively produces an increase in both CTL and T helper immune responses would be of enormous use for treatment or prophylaxis of any number of diseases, particularly viral diseases such as HCMV and HIV.

Exogenous T helper activity can be provided in trans by co-administration of the pan HLA DR-binding epitope, PADRE. The PADRE sequence is a chemically defined promiscuous T helper peptide epitope capable of binding with high affinity to a broad range of the most common HLA-DR types. Vaccines using this strategy are known to require formulation with a potent adjuvant to evoke a cytolytic response. Previously, peptide administered with DNA adjuvant has been shown to stimulate CTL in a $T_h$-independent manner, but in some cases only after repeated doses.

To produce a strong CTL response, it is usually necessary to formulate a vaccine with powerful immunological adjuvants. Unfortunately, many of the known adjuvants fail to induce antigen-specific CTL, and many have associated side effects which make them unsuitable for human use. Recently, DNA adjuvants have attracted attention as safe and effective for human use with the ability to promote CTL responses. Adjuvant activity has been associated with palindromic DNA sequences that contain unmethylated CpG dinucleotides which conform to the general consensus motif of XCGY, where X is any base except C and Y is any base except G. Increasing the number of stimulatory CpG motifs in an oligodeoxynucleotide (ODN) increases its activity, while the addition of a CpG on an end or in an unfavorable sequence context could actually reduce the degree of immune activation. Krieg et al., Nature 374:6546-6549, 1995. Elimination of the CpG dinucleotides from ODN abolish their stimulatory activity. When CpG is replaced with GpG, the ODN becomes inhibitory and antagonistic to the activity of the parent ODN. Hoe et al., J. Immunol. 171:4920-4926, 2003.

For activating human cells, the optimal motif is GTCGTT and the best CpG motif for mouse or rabbit immune cells is two 5' purines followed by the CpG dinucleotide and ending with two 3' pyrimidines. The CpG DNA directly stimulates antigen presenting cells to produce cytokines (including TNF-α, IL-1, IL-6, IL-10, IL-12 and GM-CSF) and to upregulate expression of MHC and crucial costimulatory molecules. CpG DNA also may act on B lymphocytes, inducing their proliferation and then production of IL-6 and IL-10. CpG ODN also caused enhanced cytotoxicity and enhanced IFN-γ secretion by NK cells. The effect on NK cells may be indirect, requiring the presence of adherent cells of CpG-conditioned supernatants which contain IL-12, TNF-α and Type 1 interferons.

Interspecies differences in recognition by toll-like receptors (TLR) or other immune activation recognition may result in differences in recognition of CpG motifs. For example, the mouse TLR9 molecule is preferentially activated by the CpG motif GACGTT, whereas the human TLR9 is optimally triggered by the motif GTCGTT. See Bauer et al., *Proc. Natl. Acad. Sci. USA* 98:9237-9242, 2001; Hartmann et al., *J. Immunol.* 164:1617-1624, 2000. Despite these differences, addition of a CpG ODN to a commercial hepatitis B vaccine markedly accelerated seroconversion (protective IgG antibody levels attained in 2 weeks), showing the usefulness of these types of strategies in humans. See Krieg, *Trends Immunol.* 23:64-65, 2002. CpG adjuvant activity (increased rapidity of response and higher titers, resulting in protective titers to hepatitis B in 89% of the subjects by 8 weeks) has also been shown in immunocompromised HIV-infected patients. This beneficial effect in a population with reduced response can be extended to benefit other groups such as the elderly, alcoholics and cancer patients, as well as the general population. Therefore, to add extra insurance that positive immune responses seen in the well-known mouse model systems are predictive of the same results in humans, experimentation with a human-specific or a primate- and human-specific CpG ODN sequence should confirm the techniques usefulness.

Without wishing to be bound by theory, TLR9 ligands (CpG ODN) may exert their effects by specifically and strongly stimulating plasmacytoid dendritic cells, which are thought to have an important role in T-cell self-tolerance to antigens. See Krieg, *Nat. Med.* 9(7):831-835, 2003. Adjuvants that can activate plasmacytoid dendritic cells through the TLR9 receptor may be one key to get the most out of a vaccine antigen. See Kuwana et al., *Eur. J. Immunol.* 31:2547-2557, 2001; Ferguson et al., *J. Immunol.* 168:5589-5595, 2002.

Current strategies have not yielded vaccines that induce a strong, durable CTL response which results in protection from or prevention of many diseases, including, for example HIV, HCMV and cancer, which could be useful in public health, either to prevent occurrence of disease or to promote immune attack in affected persons. Therefore, new methods of producing vaccines are needed in the art.

SUMMARY OF THE INVENTION

Accordingly, embodiments of the invention provide a conjugated vaccine molecule which comprises an antigenic peptide and a DNA oligomer. The DNA oligomer may comprise a CpG sequence, such as a phosphodiester (PO) CpG DNA or a fully phosphorothioated (PS) backbone CpG DNA or combinations thereof which include PO and PS linkages. DNA oligomers suitable for use in the invention may comprise about 8 to about 300 nucleotide bases, preferably about 15 to about 100 nucleotide bases, and most preferably about 20 to about 25 nucleotide bases. The antigenic peptide preferably comprises a CTL epitope, such as PADRE:I9V (SEQ ID NO:1), KSS:PADRE:S9L, (SEQ ID NO:2) or PADRE:I9V:K/N:S9L (SEQ ID NOs:3 and 4)(see Table XXI), and may comprise a fusion peptide comprising PADRE and a CTL peptide epitope sequence. Preferably, the antigenic peptide is about 8 to about 50 amino acid residues or more, including 75, 100 or 150 amino acid residues, or any number that can be synthesized practically using automated methods.

Yet further embodiments of the invention provide an improvement in a peptide vaccine composition which comprises conjugating the peptide to a DNA oligomer and a method of increasing the effectiveness of a peptide vaccine component which comprises conjugating the peptide to a DNA oligomer.

Preferably, the peptide portion comprises minimal cytotoxic epitopes and T-help epitopes that have been defined as immunogenic by various immunologic analyses and that provide an optimal fit into an HLA Class I or Class II molecule's peptide binding groove, depending on their type. The combination of refined peptides and DNA still function as a vaccine, and the components do not inactivate each other, which would not have been predicted a priori from first principles.

DETAILED DESCRIPTION OF THE PREFERRED EMBODIMENTS

Figure 1:
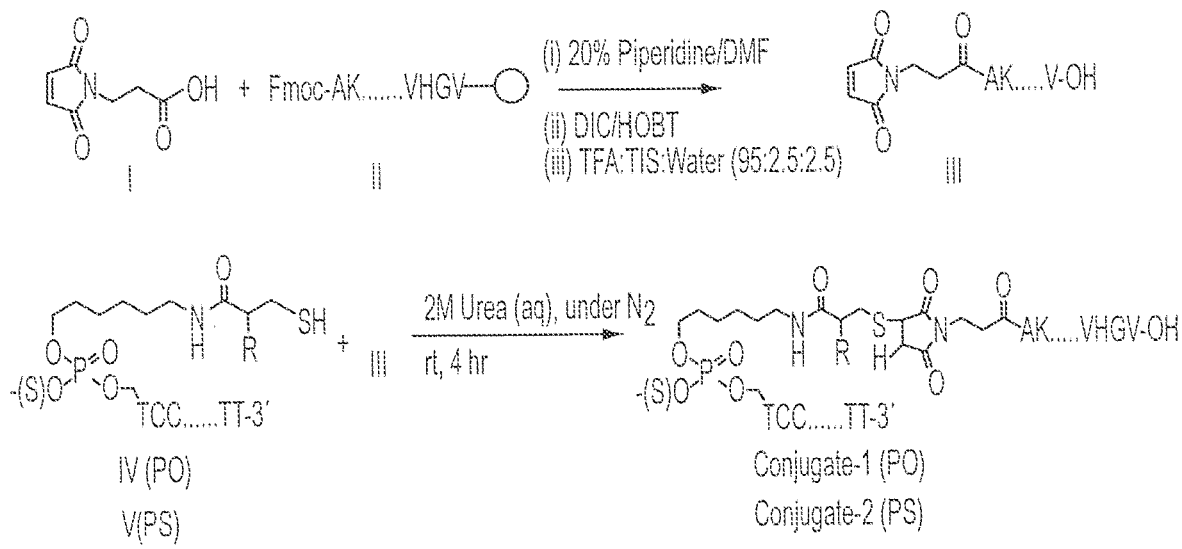
FIG. 1 shows the chemical synthetic scheme for the synthesis of Conjugates 1 and 2.

This invention provides an efficient means to immunize or vaccinate against infectious disease or any other disease treatable or preventable by vaccination, for example, HIV, HCMV and cancer. The invention involves a method of covalently attaching an antigenic peptide (for example a human cytomegalovirus, HIV or cancer antigen) to a DNA sequence that acts as an adjuvant, enhancing response to the antigen. Such DNA sequences, known as immunostimulatory nucleotide sequences, are per se known and discussed in U.S. Pat. No. 6,514,948, the disclosures of which are hereby incorporated by reference.

This invention involves covalent attachment of an immunostimulatory nucleic acid, such as a cytosine-phosphate-guanosine (CpG)-containing DNA sequence, to an antigenic peptidic sequence. The conjugates of this invention may be synthesized by reacting a DNA having a 5'-end thiohexyl modification with an N-terminal maleimide propionic acid-modified peptidic sequence to form a conjugate or by reacting DNA having a 5'-aldehyde modification to a peptide with a N-terminal hydrazine to form a conjugate linked by a hydrazone linkage. Preferred methods for their construction are illustrated in Examples 1-5. The fused vaccine compositions of this invention enhance the immune response in a mammal to the antigenic peptidic sequence and thereby increase the effectiveness of the antigen as a vaccine.

Such DNA-peptide fusions may include any DNA sequence that acts to increase immune stimulation. DNA oligomers of any source are suitable, including bacterial, viral, insect, mammalian or any source at all, including synthetic DNA molecules and DNA molecules with either phosphodiester or phosphorothioate backbones. The particular sequence contained in the DNA is not of paramount importance because any sequence can be effective to stimulate immunity according to this invention, however nucleotide sequences with CpG DNA are preferred.

In general, single-stranded DNA oligomers are used, preferably about 20 to about 25 nucleotides long, however, double-stranded DNA is contemplated for use with this invention. Double-stranded DNA conjugates can be made by first attaching single-stranded DNA to the peptide and then hybridizing the resulting conjugate to a complementary single-stranded DNA sequence. Longer or shorter DNA sequences may be used with this invention, including DNA sequences from about 8 to about 300 nucleotides long, or from about 15 to about 100 nucleotides long. Any convenient size or sequence of DNA may be used with this invention, however, it is generally preferred to use single-stranded DNA of about 10, 15, 20, 25, 30, 35, 40, or 50 nucleotides in length. DNA containing CpG sequences is preferred, but not necessary. Exemplary nucleic acids include, but are not limited to 5'-tcgtcgttttgtcgttttgtcgtt-3' (phosphorothioate-substituted; SEQ ID NO:10) and 5'-ggGGGACGATCGTCggggG-3' (in which phosphorothioate linkages are denoted by lower case letters and phosphodiester linkages by upper case letters; SEQ ID NO:11). See Hartmann et al., *J. Immunol.* 164:1617-1624, 2000. Sequences having fully phosphorothioated backbones, partially phosphorothioated backbones, or fully phosphodiester backbones are suitable.

In recent years, CpG DNA have been grouped into different classes called CpG-A and CpG-B by the Krieg group and CpG-D and CpG-K by Klinman and colleagues. See Verthelyi et al., *J. Immunol.* 166(4):2372-2377, 2001; Krug et al., *Eur. J. Immunol.* 31(7):2154-2163, 2001; Klinman et al., *Microbes. Infect.* 4(9):897-901, 2002; Gursel et al., *J. Leukoc. Biol.* 71(5):813-820, 2002. Any of these CpG sequences are suitable for use with this invention.

An ODN known to have immunologic activity is referred to as ODN 2216. This is a mixed phosphodiester-phosphorothioate backbone of the sequence ggGGGACGATCGTCggggG (SEQ ID NO:11) with small letters denoting phosphorothioate linkages and uppercase letters denoting phosphodiester linkages. This ODN is CpG A-class as defined by Krieg and collaborators. Additional motifs include pyrimidine NTTTTGT and its derivatives as described by Elias et al., *J. Immunol.* 171:3697-3704, 2003. In the context of induction of a T-helper 2 response, Tamura et al. have described ODN without CpG which function to elicit those classes of responses. These responses are not necessarily stimulatory for the types of CTL response here. Sano et al., *J. Immunol.* 170:2367-2373, 2003.

The peptide moiety of the DNA-peptide compounds according to this invention may be any antigenic peptide from any source against which enhanced immune response is desired. It is contemplated that the invention will be used most frequently with viral and bacterial antigens, particularly from bacteria and viruses that are causative agents in infectious disease. Therefore, the invention may be used to create vaccine compositions for treatment and prophylaxis of such disease as HIV, human cytomegalovirus, tuberculosis or any infections disease. Peptide epitopes of bacterial or viral origin are especially preferred. As well, cancer antigens may be used in the present invention to enhance the efficacy of cancer vaccines, for either treatment or prophylaxis.

The peptides may be of any convenient length so long as the antigenic function of the peptide is intact. Peptide CTL epitopes generally are about 8 to about 12 amino acids long, and therefore such peptides are contemplated for use with the invention and are preferred. Peptides shorter than 8 amino acids long, for example 5, 6 or 7 amino acids long, are not preferred but may be used, however longer peptide sequences are most suitable, including 9, 10, 11, 12, 13, 14, 15, 20, 25, 30, 40, 50, 100 or more amino acids in length, including multi-epitope peptides. See Alexander et al., *J. Immunol.* 168 (12):6189-6198, 2002), the disclosures of which are hereby incorporated by reference.

Fusion peptides including an antigenic peptide as described above fused to another peptide sequence are specifically contemplated for use with the inventive methods and compounds. Especially preferred peptides include fusion peptides composed of a CTL epitope sequence and a helper T lymphocyte (CD4) epitope sequence fused together. Examples of suitable CD4 epitopes include the synthetic sequence PADRE, tetanus-specific peptides, peptides derived from the same antigen or other antigens from the virus that is to be targeted. Similarly, for cancer antigens, a CD4 peptide derived from the same antigen, or any other cell-antigen known in the art, and the like may be used. Linker peptide sequences at the N- or C-terminal end of the fusion or between the CTL and CD4 epitopes in the fusion also may be used. Such linker sequences generally are from about 1 to about 10 amino acids in length and preferably are about 2 to about 7 amino acids in length or more preferably from about 3 to about 5 amino acids in length and may comprise modified or non-traditional amino acids.

Conjugate vaccine compounds may be made by providing a maleimide-substituted or hydrazine-substituted antigenic peptide of the formula

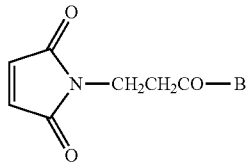

wherein B is an antigenic peptide having about 8 to about 50 or more amino acid residues; providing a 5'-end thiohexyl modified CpG DNA of the formula A-$(CH_2)_6$—SH or an aldehyde (Amidite-A™) of the formula A-Amidite™, wherein A is a CpG DNA oligomer having about 8 to about 300 nucleotide bases; reacting the peptide of step (a) and the DNA of step (b); and purifying the resulting conjugate vaccine compound of the formula

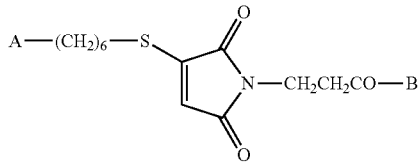

wherein B is an antigenic peptide having about 8 to about 50-100 or more amino acid residues and A is a CpG DNA oligomer having about 8 to about 300 nucleotide bases. Compounds made by this method also form part of this invention. Preferred compounds and methods are those in which the antigenic peptide is a fusion peptide comprising PADRE and a CTL peptide epitope sequence. The CpG DNA oligomer may have a phosphodiester or fully phosphorothioated backbone.

The biologic properties of peptides were studied in HLA A*0201/Kb mice. These model mice express the human HLA type and are well-known to successfully predict human clinical immune responses and demonstrate the usefulness of these molecules in modifying immunity to the antigen. The non-natural assembly of these peptide-DNA fusions was processed to result in an immunologic response with greater sensitivity of recognition compared to non-linked molecules.

All references cited herein are incorporated by reference into this specification in their entirety. In light of the preceding description, one skilled in the art can practice the invention in its full scope. The following examples, therefore, are to be construed as illustrative only and not limiting in relation to the remainder of the disclosure.

EXAMPLES

Example 1

Synthesis of Peptide-Oligonucleotide (CpG DNA) Conjugates 1 & 2

Synthesis of Conjugate 1 (a conjugate of CpG DNA Oligo 1 (SEQ ID NO:7) and PADRE:I9V fusion peptide (SEQ ID NO:1)) and Conjugate 2 (a conjugate of CpG DNA Oligo 2 (SEQ ID NO:8) and PADRE:I9V fusion peptide (SEQ ID NO:1)) was accomplished as follows. See FIG. 1.

(1) Synthesis of Mal-Peptide

All reagents were Peptide Synthesis Grade. Synthesis: Fmoc-Strategy, Manual. Wang™ Resin (substitution about 0.8 mmole/g) (Novabiochem™, San Diego, Calif.).

Fmoc-Val-OH was attached to the Wang™ resin (1 eq; substitution approximately 0.8 mmole by the symmetrical anhydride (5 eq)/DMAP (1 eq) method. The symmetrical anhydride was made using Fmoc-Val-OH and 1,3-diisopropylcarbodiimide (DIC) in a 2:1 ratio. A total of 0.4 g Fmoc-Val-Wang™ Resin (approximately 0.22 mmole) was produced. The Fmoc group was deblocked at each step of the growing peptide chain by 20% piperidine/DMF treatment. All the amino acids used during chain elongation were $N^\alpha$-Fmoc-protected, however, amino acids with side chain functionalities were used with the additional protective groups: (a) histidine modified with trityl; (b) lysine and tryptophan modified with Boc; (c) glutamic acid and threonine modified with t-butyl. Coupling of all amino acids was done using 2-(1H-benzotriazole-1-yl)-1,1,3,3-tetramethyluronium (HBTU)/DIEA reagents. Peptide chain elongation was continued using known methods to create the PADRE-I9V epitope fusion peptide (AKXVAAWTL-KAAAILKEPVHGV; X=cyclohexylalanine; SEQ ID NO:1). After deprotection of the Fmoc group from the N-terminal alanine of the peptide chain assembled on the resin, maleimide propionic acid was introduced to the free amino group of the alanine in the presence of DIC/1-hydroxybenzotriazole reagent.

The remaining protecting groups then were removed. Final cleavage was achieved by treating the peptide-linked resin with trifluoroacetic acid (TFA)/triisopropylsilane (TIS)/water (95/2.5/2.5) for two hours at room temperature. This was followed by methyl-t-butyl ether (MBTE) precipitation, filtration and drying of the product.

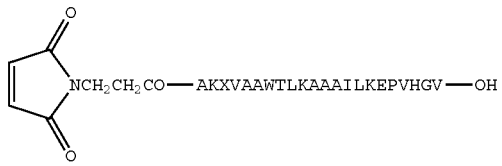

Approximately 440 mg crude product (about 40% pure Mal-peptide) of formula was obtained (X=cyclohexylalanine; SEQ ID NO:1).

Purification was performed on a Shimadzu™ HPLC System consisting of LC-8A binary pumps and a SPD-10A UV detector using a VYDAC column (22×250 mm; packing material: C-4, 10μ, 300 Å). About 440 mg crude peptide (purity about 40%) was purified in 2 lots. Each lot of about 210-220 mg was dissolved in 40 ml of 20% acetic acid/H$_2$O, filtered through a 0.45μ filter, and loaded on a pre-equilibrated column through a solenoid valve (FCV-11AL; Shimadzu™) from port B, attached to the line of LC-8A Pump-A.

With detection at a wavelength of 220 nm, one column-volume of mobile phase A (about 80 mL) was run through the column at 8 ml/minute Mobile phase A consisted of 0.05% or 0.10% TFA in water filtered through 0.2μ filter paper. A gradient of mobile phase A and mobile phase B (0.08% TFA and in acetonitrile/water (1:1)) then was run as shown in Table I, below, at 8 ml/minute.

TABLE I

HPLC Mobile Phase, Step One

| Time (min.) | Gradient Conditions | |
|---|---|---|
| | % A | % B |
| 0.01 | 80 | 20 |
| 50 | 55 | 45 |
| 60 | 0 | 100 |
| 70 | 0 | 100 |
| 70.01 | 80 | 20 |
| 80 | Stop | |

Fractions were collected. The peptide material eluted between 30 and 45 minutes. The desired fractions were pooled and subjected to analytical HPLC. The mobile phases were as described above, with a flow rate of 1 ml/minute. The column was a 4.6×250 mm C-18 column (5μ, 300 Å). After loading onto a pre-equilibrated column as described above, the gradient shown in Table II, below was run.

TABLE II

HPLC Mobile Phase, Step Two

| Time (min.) | Gradient Conditions | |
|---|---|---|
| | % A | % B |
| 0.01 | 50 | 50 |
| 25 | 0 | 100 |
| 30 | 0 | 100 |
| 30.01 | 50 | 50 |
| 39 | Stop | |

All fractions containing purified peptide were pooled and concentrated to one-third their original volume using a Rotavapor™, then freeze-dried in a pre-weighed vial. About 70 mg peptide was obtained.

This freeze-dried material was analyzed for purity using the same HPLC methodology as described above for step two and also by the following method. A sample was loaded onto a 4.6×250 mm C-4 column (5μ, 300 Å) and the gradient provided in Table III, below was run. Mobile phase C was 10% acetonitrile in 0.1 M triethylammonium acetate, pH 5.2-5.4 in water. Mobile phase D was 100% acetonitrile. By both HPLC methods, the synthetic peptide was greater than or equal to 85% pure.

TABLE III

HPLC Mobile Phase, Analysis.

| Time (min.) | Gradient Conditions | |
|---|---|---|
| | % C | % D |
| 0.01 | 100 | 0 |
| 20 | 40 | 60 |
| 25 | 40 | 60 |
| 25.01 | 100 | 0 |
| 30 | Stop | |

The synthetic peptide also was analyzed by mass spectroscopy on a Shimadzu™-Kratos™ MALDI-TOF™ Kompact Probe™ instrument. The determined mass was within the stated error of the instrument (calculated mass=2478 amu, experimental mass=2477.9 amu).

Oligo 1 (phosphodiester single-stranded CpG DNA (5'-tccatgacgttcctgacgtt-3'; SEQ ID NO:7), with the 5' end modified to thiohexyl) and Oligo 2 (fully phosphorothioated backbone, single-stranded CpG DNA (5'-tccatgacgttcct-gacgtt-3' (SEQ ID NO:8) with the 5' end modified to thiohexyl, (—(CH$_2$)$_6$—S—H) were analyzed by analytical HPLC according to method B above and found to be about 85% and 60% pure, respectively. The DNAs each were dissolved in 6.5 ml 0.1 M triethylammonium acetate, pH 7.0.

Synthesis of Conjugate 1

The conjugate reaction was carried out between PADRE: I9V (SEQ ID NO:1) and Oligo 1 above. All reagents were DNA synthesis grade. The peptide (5.0 mg, 2 eq) was dissolved in 0.1 M guanidine hydrochloride solution (5 mL), pH 6.5-7.0. Oligo 1(6.5 mg, 1 eq) was dissolved in 0.1 M TEAA (6.5 mL), pH 7.0. The above two solutions were mixed together under N$_2$ atmosphere and stirred for 4 hours at room temperature. The reaction mixture was filtered through a 0.45μ filter and passed through the preparative HPLC C-4, 10×250 mm, column for desalting and purification (flow rate=4 mL/min; λ=260 nm; mobile phase A=10% ACN, 0.1M, TEAA, pH 5.2-5.4; mobile phase B=ACN). Mobile phase A and B were filtered through 0.2μ filter paper. The column was equilibrated with one column volume (about 20 mL) mobile phase A. After loading the sample, the column was desalted with one column volume (about 20 mL). The desired product was eluted using the following gradient. See Table IV.

TABLE IV

HPLC Mobile Phase, Synthetic Conjugate

| Time (min.) | Gradient Conditions | |
|---|---|---|
| | % E | % D |
| 0.01 | 100 | 0 |
| 30 | 40 | 60 |
| 35 | 40 | 60 |
| 35.01 | 0 | 100 |
| 45 | 0 | 100 |
| 45 | Stop | |

The desired peak eluted at between 20-30 minutes of the gradient run. The peak was collected and concentrated on a Rotavapor™ to ⅓ of its original volume, then freeze dried in a pre-weighed vial. About 3.0 mg of Conjugate 1 was obtained. The product was analyzed by HPLC using Method B as above and 8 M urea, 15% acrylamide PAGE as follows.

Figure 2:
FIG. 2 is a polyacrylamide gel. Lane 1=Oligo 1; lane 2=Oligo 2; lane 3=Conjugate 1; lane 4=Conjugate 2; lane 5=the maleimide propionic addition product of AKXVAAW-TLKAAAILKEPVHGV (X=cyclohexylalanine; SEQ ID NO:1).

The gel was run at 250 V for 30 minutes. The sample (10 μL) was prepared in formamide, heated to 70₀C for 5 minutes and loaded onto the gel with bromophenol blue tracking dye. The gel then was run at 250 V for about thirty minutes until the dye reached the bottom. The gel was stained using Gel Code Blue™ Stain Reagent. See FIG. 2.

Synthesis of Conjugate 2

The conjugate reaction was carried out between PADRE: I9V peptide (SEQ ID NO:1) and Oligo 2. Peptide (2.5 mg, 1 eq) was dissolved in 2 M urea (5 mL). Oligo 2 (6.5 mg, 1 eq) was dissolved in 2 M urea (6.5 mL). The above two solutions were mixed together under $N_2$ atmosphere and stirred for four hours at room temperature. The reaction mixture was filtered through a 0.45μ filter and passed through a preparative HPLC column for desalting and purification: flow rate=4 mL/minute; λ=260 nm; mobile phase A=10% ACN, 0.1 M TEAA, pH 5.2-5.4; mobile phase B=ACN. Mobile phases A and B were filtered through a 0.2μ (Millipore) filter paper. The column was equilibrated with one column volume (about 20 mL) and the sample was loaded, then desalted with one column volume (about 20 mL). The gradient below was used to elute the desired product at between 20-30 minutes.

TABLE V

HPLC Mobile Phase

| Time (min.) | Gradient Conditions | |
|---|---|---|
| | % A | % B |
| 0.01 | 100 | 0 |
| 30 | 40 | 60 |
| 35 | 40 | 60 |
| 35.01 | 0 | 100 |
| 45 | 0 | 100 |
| 45 | Stop | |

The desired peak was collected and concentrated on a Rotavapor™ to ⅓ of its original volume, then freeze-dried in a pre-weighed vial. About 2.0 mg of Conjugate 2 was obtained. The product was analyzed by HPLC according to Method B (70-80% pure), and by PAGE according to Method C and produced a single band. See FIG. 2.

Example 2

Synthesis of Peptide—Oligonucleotide (CpG DNA) Conjugate 3

Figure 3:
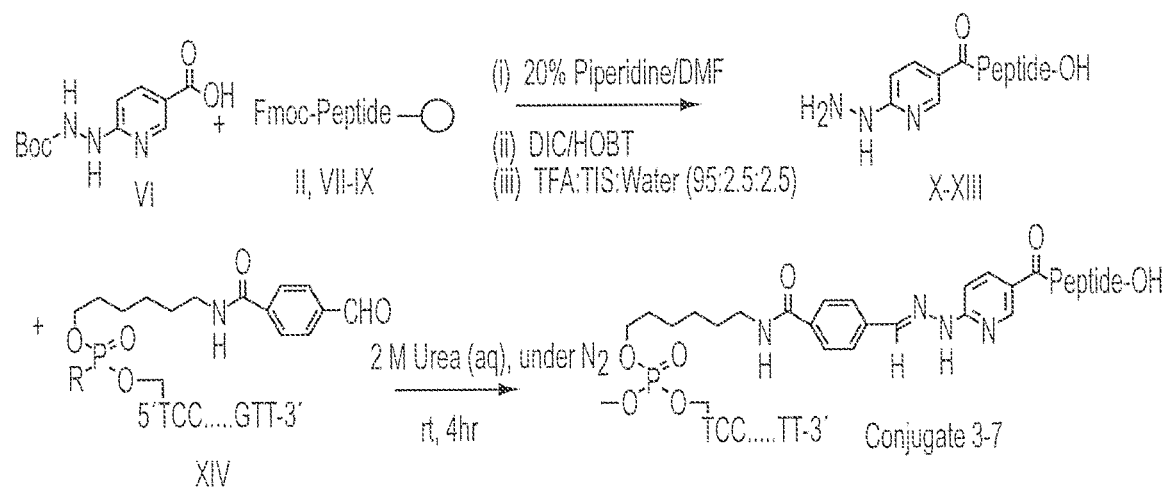
FIG. 3 shows the chemical synthetic scheme for the synthesis of Conjugates 3-7.

Synthesis and purification of Hyd-PADRE:I9V (SEQ ID NO:1) conjugate with a fully phosphorothioated backbone, single-stranded CpG DNA (5'-tccatgacgttcctgacgtt-3'; SEQ ID NO:9) with 5' end modified to aldehyde, obtained from Trilink Technologies™ and referred to as Oligo 3, was accomplished as follows. All the reagents were peptide synthesis grade. Fmoc-Val-OH (>99%) was attached to the Wang™ resin (substitution about 0.8 mmole/g; 1 eq) by the symmetrical anhydride (5 eq)/DMAP (1 eq) method. Synthesis proceeded as using Fmoc-Val-OH and DIC in a 2:1 ratio. See FIG. 3.

Synthesis was started with 0.4 g Fmoc-Val-Wang™ resin (approximately 0.22 mmole). The Fmoc group was deblocked at each step of the growing peptide chain by 20% piperidine/DMF treatment. All the amino acids used during chain elongation were $N^{\alpha}$-Fmoc-protected, however amino acids with side chain functionalities were used with the additional protective groups: (histidine modified with trityl; lysine and tryptophan modified with Boc; glutamic acid and threonine modified with t-butyl). Coupling of all amino acids was done using HBTU/DIEA reagents. After deprotection of the Fmoc group from the N-terminal alanine of the peptide chain assembled on the resin, HDA was introduced to the free amino group of alanine in the presence of DIC/1-hydroxybenzotriazole reagent. Final cleavage was done by treating peptide-resin with TFA/TIS/water in a 95/2.5/2.5 ratio for two hours at room temperature. This was followed by MBTE precipitation, filtration and drying of the product. Approximately 440 mg of crude product (about 40% purity by analytical HPLC, Method A) was obtained.

Purification was done on Shimadzu™ HPLC system with LC-8A binary pumps and SPD-10A UV Detector, using a VYDAC column (22×250 mm; packing material, C-4, 10μ, 300 Å). About 440 mg crude peptide (purity about 40%) was purified in 2 lots. Each lot of about 210-220 mg was dissolved in 40 ml of 20% acetic acid/$H_2O$, filtered through a 0.45μ filter, and loaded on a pre-equilibrated column through the solenoid valve FCV-11AL from port B, attached to the line of LC-8A Pump-A (flow rate=8 mL/minute; λ=220 nm; mobile phase=0.05% TFA, $H_2O$; acetonitrile). Mobile phases A and B were filtered through 0.2μ filter paper. The column was equilibrated with one column volume of mobile phase A (about 80 mL) and the sample loaded. One column volume of mobile phase A (about 80 mL) was followed by the gradient below.

TABLE VI

HPLC Mobile Phase

| Time (min.) | Gradient Conditions | |
|---|---|---|
| | % A | % B |
| 0.01 | 80 | 20 |
| 50 | 55 | 45 |
| 60 | 0 | 100 |
| 70 | 0 | 100 |
| 70.01 | 80 | 20 |
| 80 | Stop | |

The desired peak eluted between 30 and 45 minutes of the gradient. The fractions were analyzed by analytical HPLC according to Method A: flow rate=1 mL/minute; λ=220 nm, column=C-18, 5μ, 300 Å, 4.6×250 mm; mobile phase A=0.10% TFA, $H_2O$; mobile phase B=0.08% TFA, 1:1 ACN/$H_2O$.

TABLE VII

HPLC Mobile Phase

| Time (min.) | Gradient Conditions | |
|---|---|---|
| | % A | % B |
| 0.01 | 50 | 50 |
| 25 | 0 | 100 |
| 30 | 0 | 100 |
| 30.01 | 50 | 50 |
| 39 | Stop | |

All the fractions containing pure peptide (≥85%) from all the four lots were pooled and concentrated on a Rotavapor™ to ⅓ of its original volume, then freeze-dried in a pre-weighed vial. About 80 mg of peptide was obtained. This freeze dried material was again analyzed by analytical HPLC and mass analysis by method A above and method B: flow rate=1 mL/minute; λ=260 nm; column=C-4, 5 300 Å, 4.6×250 mm; mobile phase A=10% acetonitrile, 0.1 M TEAA, pH 5.2-5.4; mobile phase B=ACN.

TABLE VIII

HPLC Mobile Phase

| Time (min.) | Gradient Conditions | |
|---|---|---|
| | % A | % B |
| 0.01 | 100 | 0 |
| 20 | 40 | 60 |
| 25 | 40 | 60 |
| 25.01 | 100 | 0 |
| 0 | Stop | |

Mass analysis was carried out on a Shimadzu™-Kratos™ MALDI-TOF™ Kompact Probe™ mass analyzer. The calculated mass was 2462 a.m.u. The experimental mass was 2462 a.m.u., which is within the stated error of the instrument.

CpG-DNA fully phosphorothioated with 5'-end modified to aldehyde (Oligo 3) was obtained from Trilink Technologies™, analyzed by analytical HPLC as per Method B above and found to be ≥60% pure.

Synthesis of Conjugate 3

The peptide above, PADRE:I9V (SEQ ID NO:1; 4.2 mg, about 1.7 eq), was dissolved in 2 M urea solution (5 mL). Oligo 3 (SEQ ID NO:8; 13.4 mg, about 2 eq) was dissolved in 2 M urea (15 mL). The above two solutions were mixed together and stirred for three hours at room temperature. The reaction mixture was filtered through a 0.45µ filter and passed through the preparative HPLC C-4, column (22×250 mm) for desalting and purification: (flow rate=8 mL/minute; λ-260 nm; mobile phase A=10% ACN, 0.1 M TEAA, pH 5.1-5.2; mobile phase B=ACN). Mobile phases A and B were filtered through a 0.2µ filter paper. The column was equilibrated with one column volume (about 80 mL) of mobile phase A and the sample loaded. One column volume (about 80 mL) was run through the column for desalting. The following gradient was used to elute the desired product.

TABLE IX

HPLC Mobile Phase

| Time (min.) | Gradient Conditions | |
|---|---|---|
| | % A | % B |
| 0.01 | 100 | 0 |
| 50 | 50 | 50 |
| 50.01 | 0 | 100 |
| 60 | Stop | |

Figure 4:
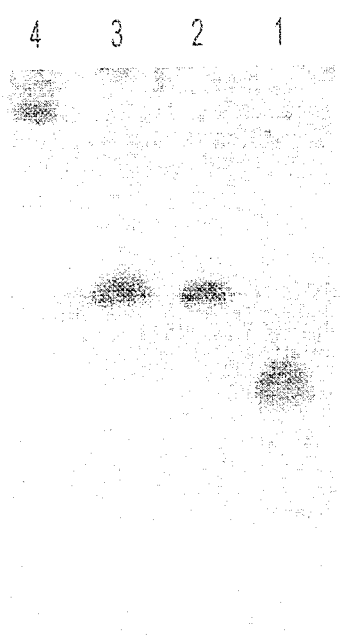
FIG. 4 is a polyacrylamide gel. Lane 1=Oligo 3; lane 2=Conjugate 2; lane 3=Conjugate 3; lane 4=Hyd-PADRE: I9V (AKXVAAWTLKAAAILKEPVHGV; X=cyclohexylalanine; SEQ ID NO:1).

The desired peak eluted between 35-45 minutes of gradient run. The peak collected above was concentrated on a Rotavapor™ to ⅓ of its original volume and then freeze dried in a pre-weighed vial. About 5.1 mg of Conjugate 3 was obtained. The product was analyzed by HPLC by Method B above and found to be 70-80% pure. Under PAGE, a single band was found using Method C: gel, 8 M urea, 15% acrylamide; pre-run at 250 V for 30 minutes; sample run, 10 µL sample formamide, heated to 70°C for five minutes and loaded; tracking dye, bromophenol blue; run at 250 V until tracking dye reaches bottom (about 30 minutes). The gel was stained with Gel Code Blue™ Stain-Reagent. See FIG. 4.

Synthesis of Conjugate 3 (Batch-2)

All reagents were DNA synthesis grade. Hyd-PADRE: I9V (SEQ ID NO:1; 4.1 mg, about 1.7 eq) was dissolved in 2 M urea solution (5 mL). Oligo 3 (SEQ ID NO:8; 13.5 mg, about 2 eq) was dissolved in 2 M urea (15 mL). The above two solutions were mixed together and stirred for three hours at room temperature. The reaction mixture was filtered through a 0.45µ filter and passed through the preparative HPLC diphenyl column (10×250 mm) for desalting and purification: flow rate=4 mL/minute; λ=260 nm; mobile phase A=10% ACN, 0.1 M TEAA, pH 5.1-5.2; mobile phase B=ACN. Mobile phases A and B were filtered through a 0.2µ filter paper. The column was equilibrated with one column volume (about 20 mL) of mobile phase A and the sample loaded. One column volume (about 20 mL) was run through the column for desalting. The gradient below was used to elute the desired product.

TABLE X

HPLC Mobile Phase

| Time (min.) | Gradient Conditions | |
|---|---|---|
| | % A | % B |
| 0.01 | 100 | 0 |
| 40 | 40 | 60 |
| 45 | 0 | 100 |
| 60 | Stop | |

The desired peak eluted between 20-30 minutes of the gradient run. The peak collected above was concentrated on Rotavapor™ to ⅓ of its original volume and then freeze dried in a pre-weighed vial. About 7.0 mg of Conjugate 3 was obtained. The product was analyzed by HPLC by Method B above, using a diphenyl column, in place of the C-4 column and found to be ≥70-80% pure. The material formed a single band by PAGE, Method C.

Figure 5:
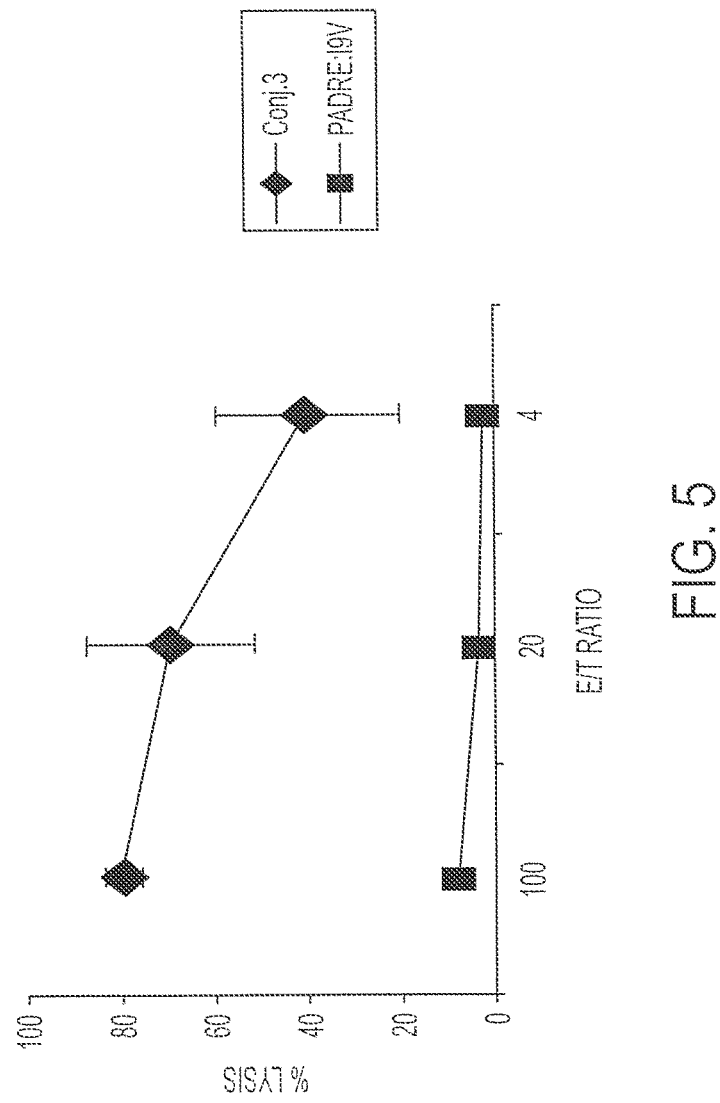
FIG. 5 shows percent lysis by splenocytes immunized once with 1 nmole Conjugate 3 or 50 nmole PADRE:I9V (AKXVAAWTLKAAAILKEPVHGV; X=cyclohexylalanine; SEQ ID NO:1) P (T≤t) two-tail 0.03.

To demonstrate that the conjugate molecules are immunogenic, HLA A2/kb mice were immunized once subcutaneously with 1 nmole Conjugate 3. Fourteen days later, the spleens were retrieved. The CTL responses of the immune splenocytes were tested after one round of in vitro stimulation (IVS). FIG. 5 shows that administration of a single dose of 1 nmole Conjugate 3 results in 80% target cell lysis at an E:T ratio of 100, while administration of two doses of 50 nmoles PADRE:I9V fusion peptide (unconjugated; AKXVAAWTLKAAAILKEPVHGV; X=cyclohexylalanine; SEQ ID NO:1) resulted in only 8% cell lysis at the same E:T ratio. Targets were labeled with I9V peptide (SEQ ID NO:5) for both sets of animals. This demonstrates the ability of Conjugate 3 to be processed and to induce specific CTL responses. This experiment was repeated four times with similar results each time. Using a two-tailed T test, there was a significant difference of P<0.03 at all E:T ratios. An additional analysis using flow cytometry revealed that high frequencies of splenic T cells were stimulated by the incubation with the I9V peptide to produce IFN-γ. This IFN-γ-producing population is present only after stimulation with the specific I9V peptide. Consistently, between 5 and 60% of the CD8$^+$ T cell population were specific for I9V after immunization with Conjugate 3.

Example 3

Synthesis of Peptide-Oligonucleotide (CpG DNA) Conjugate 4

Figure 6:
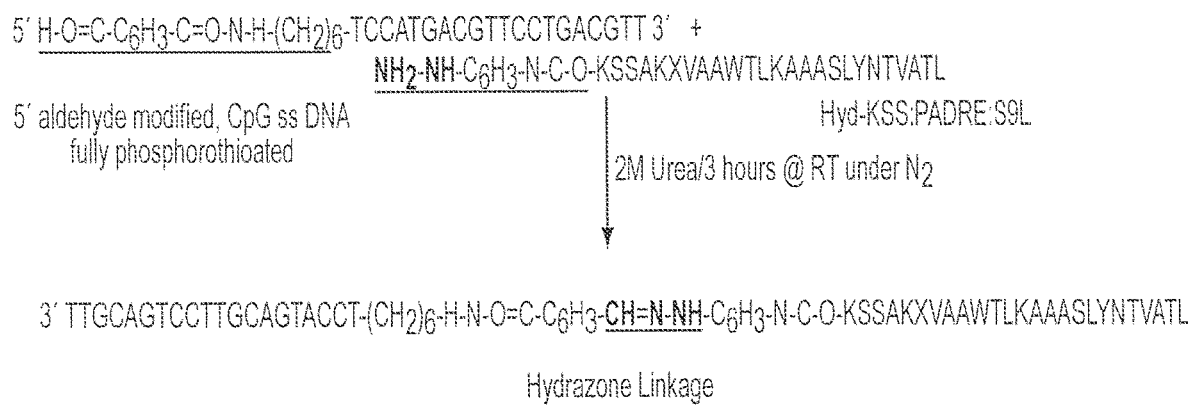
FIG. 6 shows a partial synthetic scheme for synthesis of Conjugate 4 (SEQ ID NOs:2 and 9).

Synthesis and purification of Hyd-KSS:PADRE: S9L; KSSAKXVAAWTLKAAASLYN TVATL; X=cyclohexylalanine; (SEQ ID NO:2; PADRE-HIVgag fusion) was performed as follows. Fully phosphorothioated backbone, single-stranded (ss) CpG DNA (5'-CHO—$C_6H_5$—(CONH—($CH_5$—(CONH—($CH_2$)$_6$—O-tcctgacgt-tcctgacgtt –3'; SEQ ID NO:9) with 5' end modified to aldehyde was obtained from Trilink Technologies™ and termed Oligo 3 in the text. See FIGS. 3 and 6.

Synthesis of Conjugate 4

The Conjugate reaction was carried out between Hyd-KSS:PADRE:S9L and 5'-aldehyde substituted oligonucleotide with phosphorothioated backbone i.e. Oligo 3.

Synthesis of Hyd-KSS:PADRE:S9L

All the reagents were Peptide Synthesis Grade. Synthesis: Fmoc-Strategy, Manual. Wang™ resin (substitution about 0.8 mmole/g). Fmoc-Leu-OH (>99%) was attached to the Wang™ resin (1 eq) by the symmetrical anhydride (5 eq)/DMAP (1 eq) method as described above (symmetrical anhydride was made using Fmoc-Val-OH and DIC in a 2:1 ratio. Synthesis was started with 0.4 g Fmoc-Leu-Wang™ resin (approximately 0.22 mmole). The Fmoc-group was deblocked at each step of the growing peptide chain by 20% piperidine/DMF treatment. All the amino acids used during chain elongation were $N^\alpha$-Fmoc-protected, however, amino acids with side chain functionalities were used with additional protective groups: asparagine modified with trityl; lysine and tryptophan modified with Boc; tyrosine, serine and threonine modified with t-butyl. Coupling of all amino acids was done using HBTU/DIEA reagents. After deprotection of the Fmoc-group from the N-terminal lysine of the peptide chain assembled on the resin, HDA (1 eq) was introduced to the free alpha amino group of lysine in the presence of DIC/1-hydroxybenzotriazole reagent. Final cleavage was done by treating the peptide-resin with TFA/thioanisole/ethanedithiol/water in a 90/5/2.5/2.5 ratio (2 hour treatment) at room temperature. This was followed by MTBE precipitation, filtration and drying of the product. Approximately 400 mg of crude product (about 40% Purity, analyzed by analytical HPLC, Method A) was obtained.

Purification of Hyd-Peptide

Purification was done on Shimadzu™ HPLC system consisting of LC-8A binary pumps and an SPD-10A UV Detector, using VYDAC column (22×250 mm; packing material, C-4, 10µ, 300 Å). About 400 mg crude peptide (purity about 40%) was purified in 2 lots. About 200 mg was dissolved in 40 mL 20% acetic acid/$H_2O$, filtered through a 0.45µ filter, and loaded onto a pre-equilibrated column through a solenoid valve FCV-11AL (Shimadzu™) from port B, attached to the line of LC-8A Pump-A: flow rate=8 mL/minute; λ=220 nm; mobile phase=0.05% TFA, $H_2O$; acetonitrile (ACN). Mobile phases A and B were filtered through a 0.2µ filter paper. The column was equilibrated with one column volume of mobile phase A (about 80 mL) and the sample was loaded as above. One column volume of Mobile Phase A (about 80 ml) was run through the column, followed by the gradient below.

TABLE XI

| HPLC Mobile Phase | | |
|---|---|---|
| | Gradient Conditions | |
| Time (min.) | % A | % B |
| 0.01 | 80 | 20 |
| 50 | 55 | 45 |
| 60 | 0 | 100 |
| 70 | 0 | 100 |
| 70.01 | 80 | 20 |
| 80 | Stop | |

The desired peak eluted between 30 and 45 minutes of the gradient run. The fractions were analyzed by analytical HPLC as per Method A: flow rate=1 mL/minute; λ, =220 nm; column=C-18, 5µ 300 Å, 4.6×250 mm; mobile phase A=0.10% TFA, $H_2O$; mobile phase B=0.08% TFA, 1:1 ACN/$H_2O$.

TABLE XII

| HPLC Mobile Phase | | |
|---|---|---|
| | Gradient Conditions | |
| Time (min.) | % A | % B |
| 0.01 | 50 | 50 |
| 25 | 0 | 100 |
| 30 | 0 | 100 |
| 30.01 | 50 | 50 |
| 39 | Stop | |

All the fractions containing pure peptide (≥85%) from all the four lots were pooled and concentrated on a Rotavapor™ to ⅓ of its original volume, then freeze-dried in a pre-weighed vial. About 60 mg of peptide was obtained. This freeze dried material was analyzed by analytical HPLC (method A above and method B below) and mass analysis. Mass analysis was carried out on Shimadzu-Kratos™ MALDI-TOF™ Kompact Probe™ mass analyzer. The calculated mass was 2754 a.m.u. and the experimental mass was 2754.4 a.m.u., which is within the stated error of the instrument. HPLC method B: flow rate=1 mL/minute; λ=260 nm; column=diphenyl, 5µ, 300 Å, 4.6×250 mm; mobile Phase A=10% ACN, 0.1 M TEAA, pH 5.0-5.1; mobile phase B=ACN.

TABLE XIII

| HPLC Mobile Phase | | |
|---|---|---|
| | Gradient Conditions | |
| Time (min.) | % A | % B |
| 0.01 | 100 | 0 |
| 20 | 40 | 60 |
| 25 | 40 | 60 |
| 25.01 | 100 | 0 |
| 0 | Stop | |

Oligo 3

CpG-DNA fully phosphorothioated with 5'-end modified to aldehyde (CHO) was obtained from Trilink Technologies™, analyzed by analytical HPLC by method B above and found to be about 60% pure.

Synthesis of Conjugate 4

All the reagents were DNA synthesis grade. Hyd-KSS-PADRE:S9L (SEQ ID NO:2; 4.7 mg, about 1.7 eq) was dissolved in 2 M urea solution (5 mL). Oligo 3 (14.7 mg, about 2.2 eq) was dissolved in 2 M Urea (15 mL). The two solutions were mixed together and stirred for 3 hours at room temperature. The reaction mixture was filtered through a 0.45µ filter and passed through a preparative HPLC diphenyl column (10×250 mm) for desalting and purification: flow rate=4 mL/min; λ=260 nm; mobile phase A=10% ACN, 0.1 M TEAA, pH 5.0-5.1; mobile phase B=ACN. Mobile phases A and B were filtered through 0.2µ filter paper. The column was equilibrated with one column volume (about 20 mL) mobile phase A, and the sample was loaded. One column volume (about 20 mL) was run through the column for desalting. The gradient below was used to elute the desired product.

TABLE XIV

HPLC Mobile Phase

| Time (min.) | Gradient Conditions | |
|---|---|---|
| | % A | % B |
| 0.01 | 100 | 0 |
| 40 | 40 | 60 |
| 45 | 0 | 100 |
| 60 | Stop | |

Figure 7:
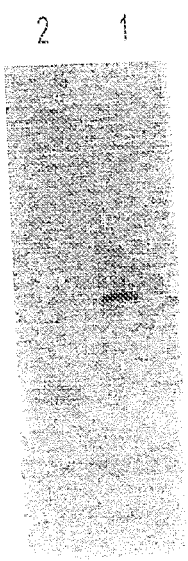
FIG. 7 is a polyacrylamide gel. Lane 1=Oligo 3; lane 2=Conjugate 2.

The desired peak eluted between 20-30 minutes of the gradient run. The desired peak collected above was concentrated on a Rotavapor™ to ⅓ of its original volume and then freeze dried in a pre-weighed vial. About 6.0 mg of Conjugate 4 was obtained. This product was analyzed by HPLC (about 70-80% pure by method B above) and by PAGE (forming a single band by method C: gel preparation, 8 M urea, 15% acrylamide; pre-run, 250 V for 30 minutes; sample run, 10 µL sample formamide, heated to 70$_c$C for 5 minute and loaded, tracking dye, bromophenol; run, 250 V for about 30 minutes or until the dye reached the bottom; staining, Gel Code Blue™ Stain Reagent. See FIG. 7.

Example 4

Synthesis of Peptide-Oligonucleotide (CpG DNA) Conjugate 5

Figure 8:
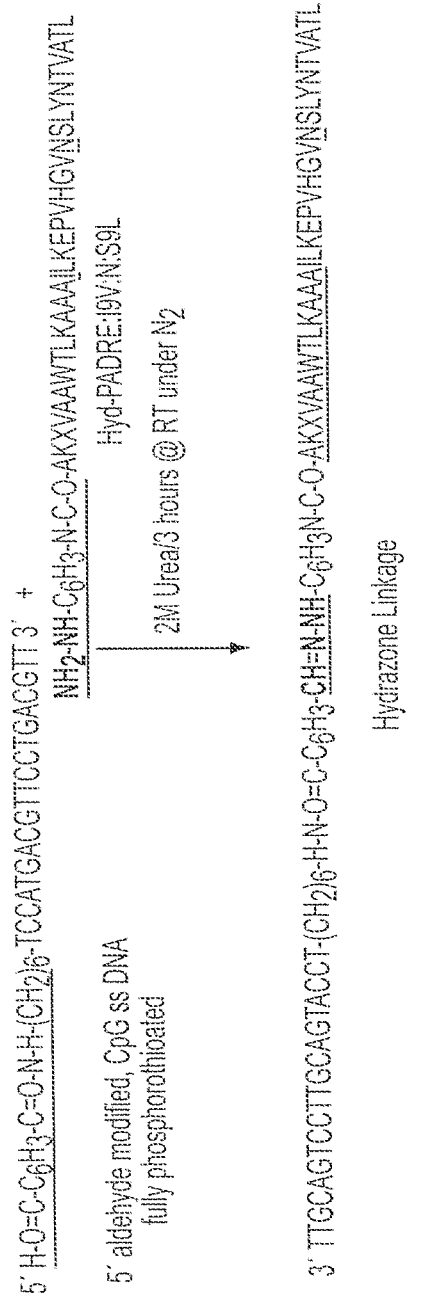
FIG. 8 shows a partial synthetic scheme for synthesis of Conjugate 5 (SEQ ID NOs:4 and 9).

Synthesis and purification of Hyd-PADRE:I9V:N:S9L (AKXVAAWTLKAAAILK EPVHGVNSLYNTVATL; X=cyclohexylalanine; SEQ ID NO:4; PADRE-HIVpol-Asn-HIVgag fusion) was performed as follows. Fully phosphorothioated backbone, single-stranded CpG DNA (5'-3' tccatgacgttcctgacgtt; SEQ ID NO:9) with 5' end modified to aldehyde (CHO) was obtained from Trilink Technologies™ and is termed Oligo 3. The conjugate reaction was carried out between Hyd-PADRE:I9V:N:S9L (SEQ ID NO:4) and Oligo 3. See FIG. 8.

Synthesis of Hyd-PADRE:I9V:N:S9L

All the reagents were Peptide Synthesis Grade. Synthesis: Fmoc-Strategy, manual, using Wang™ resin (substitution about 0.8 mmole/g. Fmoc-Leu-OH (>99%) was attached to the Wang™ resin (1 eq) by the symmetrical anhydride (5 eq)/DMAP (1 eq) method as described above. The symmetrical anhydride was made using Fmoc-Val-OH and DIC in a 2:1 ratio. The synthesis was started with 0.4 g Fmoc-Leu-Wang™ resin (approximately 0.22 mmole). The Fmoc group was deblocked at each step of the growing peptide chain by 20% piperidine/DMF treatment. All the amino acids used during chain elongation were N$^α$-Fmoc-protected, however, amino acids with side chain functionalities were used with the following additional protective groups: asparagine and histidine modified with trityl; lysine and tryptophan modified with Boc; glutamic acid, tyrosine, serine and threonine modified with t-butyl. Coupling of all amino acids was done using HBTU/DIEA reagents. After deprotection of the Fmoc-group from the N-terminal alanine of the peptide chain assembled on the resin, HDA (1 eq) was introduced to the free amino group of alanine in the presence of DIC/HOBt reagent.

Final cleavage was achieved by treating the peptide-resin with TFA/thioanisole/EDT/water in a 90/5/2.5/2.5 ratio (2 hour treatment) at room temperature. This was followed by MTBE precipitation, filtration and drying of the product. Approximately 450 mg of crude product (about 30% purity as determined by analytical HPLC, method A) was obtained. Purification was achieved using a Shimadzu™ HPLC system consisting of LC-8A binary pumps and a SPD-10A UV detector, using a VYDAC column (2×250 mm; packing material, C-4, 10µ, 300 Å) Sample was prepared as follows. Four hundred fifty milligrams crude peptide (purity about 40%) was purified in 2 lots. For each lot, 220-230 mg peptide was dissolved in 40 mL of 20% acetic acid/H$_2$O and filtered through 0.45µ filter, then loaded on a pre-equilibrated column through a solenoid valve FCV-11AL (Shimadzu™) from port B, attached to the line of LC-8A Pump-A: flow rate=8 mL/minute; λ=220 nm; mobile phase A, 0.05% TFA, H$_2$O; mobile phase B, ACN. Mobile phases A and B were filtered through 0.2µ filter paper. One column volume of Mobile Phase A (about 80 mL) was used to equilibrate the column. The sample was loaded as described above. One column volume of mobile phase A (about 80 mL) was run through the column for desalting, followed by the gradient below.

TABLE XV

HPLC Mobile Phase

| Time (min.) | Gradient Conditions | |
|---|---|---|
| | % A | % B |
| 0.01 | 87 | 13 |
| 50 | 62 | 38 |
| 60 | 0 | 100 |
| 70 | 0 | 100 |
| 70.01 | 87 | 13 |
| 80 | Stop | |

The desired peak eluted between 40 and 55 minutes of the gradient run. The collected fractions were analyzed by analytical HPLC per method A: flow rate=1 mL/minute; λ=220 nm; column=C-18, 5µ300 Å, 4.6×250 mm; mobile phase A=0.10% TFA, H$_2$O; mobile phase B=0.08% TFA, 1:1 ACN/H$_2$O.

TABLE XVI

HPLC Mobile Phase

| Time (min.) | Gradient Conditions | |
|---|---|---|
| | % A | % B |
| 0.01 | 50 | 50 |
| 25 | 0 | 100 |

TABLE XVI-continued

HPLC Mobile Phase

| Time (min.) | Gradient Conditions | |
|---|---|---|
| | % A | % B |
| 30 | 0 | 100 |
| 30.01 | 50 | 50 |
| 39 | Stop | |

All fractions containing pure peptide 85%) from all the four lots were pooled and concentrated on a Rotavapor™ to ⅓ of its original volume, then freeze-dried in a pre-weighed vial. About 60 mg of peptide was obtained. This freeze dried material was analyzed by analytical HPLC (method A above and method B below) and mass analysis using a Shimadzu-Kratos™ MALDI-TOF™ Kompact Probe™ mass analyzer.

The calculated mass was 3539 a.m.u. and the experimental mass was 3539.2 a.m.u., which is within the stated error of the instrument. Method B: flow rate=1 mL/minute; $\lambda$=260 nm; column=diphenyl, 5μ, 300 Å, 4.6×250 mm; mobile phase A=10% ACN, 0.1 M TEAA, pH 5.0-5.1; mobile phase B=ACN.

TABLE XVII

HPLC Mobile Phase

| Time (min.) | Gradient Conditions | |
|---|---|---|
| | % A | % B |
| 0.01 | 100 | 0 |
| 20 | 40 | 60 |
| 25 | 40 | 60 |
| 25.01 | 100 | 0 |
| 0 | Stop | |

Oligo 3

CpG-DNA fully phosphorothioated with 5'-end modified to aldehyde was obtained from Trilink Technologies™, analyzed by analytical HPLC by Method B above and found to be 60% pure.

Synthesis of Conjugate 5

All the reagents were DNA synthesis grade. Hyd-PADRE:I9V:N:S9L (SEQ ID NO:4; 7.2 mg, about 2 eq) was dissolved in 2M urea solution (7 mL). Oligo 3 (17.0 mg, about 2.5 eq) was dissolved in 2 M urea (17 mL). The two solutions were mixed together and stirred for 3 hours at room temperature. The reaction mixture was filtered through a 0.45μ filter and passed through the preparative HPLC diphenyl column (10×250 mm) for desalting and purification: flow rate=4 mL/min; $\lambda$=260 nm; mobile phase A=10% ACN, 0.1 M TEAA, pH 5.0-5.1; mobile phase B=ACN. Mobile phases A and B were filtered through 0.2μ filter paper. The column was equilibrated with one column volume (about 20 mL) of mobile phase A and the sample loaded. One column volume (about 20 mL) was run through the column for desalting. The following gradient then was used to elute the desired product.

TABLE XVIII

HPLC Mobile Phase

| Time (min.) | Gradient Conditions | |
|---|---|---|
| | % A | % B |
| 0.01 | 100 | 0 |
| 40 | 40 | 60 |
| 45 | 0 | 100 |
| 60 | Stop | |

Figure 9:
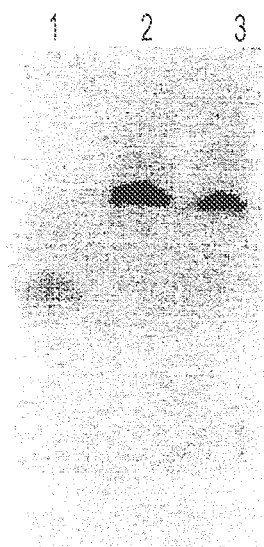
FIG. 9 is a polyacrylamide gel. Lane 1=Oligo 3; lane 2=Conjugate 6; lane 3=Conjugate 5.

The desired peak eluted between 20-32 minutes of the gradient run. The peak collected above was concentrated on a Rotavapor™ to ⅓ of its original volume and then freeze dried in a pre-weighed vial. About 8.0 mg of Conjugate 5 was obtained. The product was analyzed by HPLC 70-80% pure by method B above) and by PAGE (method C), where it ran as a single band. Method C: 8 M urea, 15% acrylamide gel; pre-run at 250 V for 30 minutes; Samples prepared with 10 μL sample formamide, heated to $70_oC$ for 5 minutes and loaded with bromophenol blue tracking dye. The gel was run at 250 V for about 30 minutes or until the dye reached the bottom. Staining was done with Gel Code Blue™ StainReagent. See FIG. 9.

Example 5

Synthesis of Peptide-Oligonucleotide (CpG DNA) Conjugate 6

Figure 10:
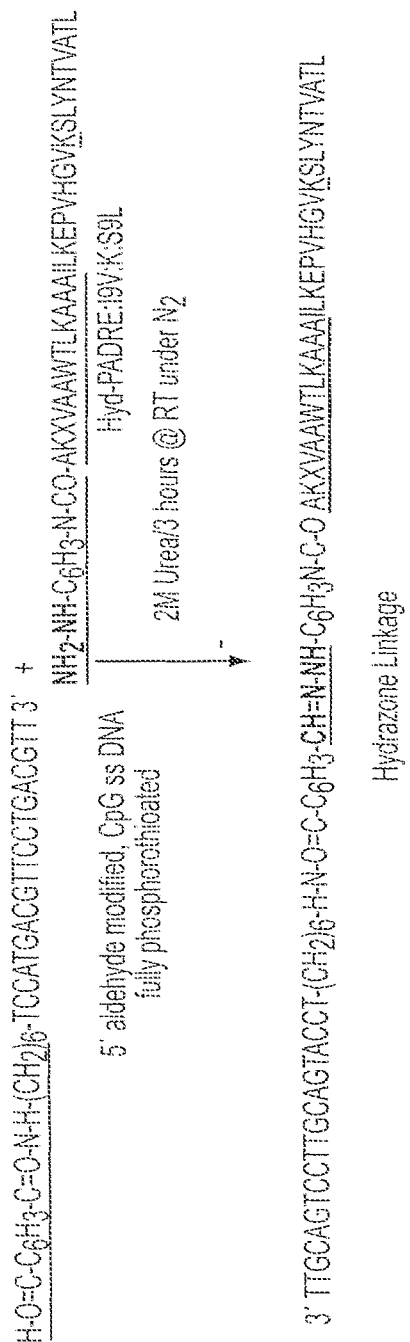
FIG. 10 shows a partial synthetic scheme for synthesis of Conjugate 6 (SEQ ID NOs:3 and 9).

Synthesis and purification of Hyd-PADRE:I9V:K:S9L (AKXVAAWTLKAAAILKEPV HGVKSLYNTVATL; SEQ ID NO:3). The conjugate reaction carried out between Hyd-PADRE:I9V:K:S9L and Oligo 3 (described above). See FIG. 10.

Synthesis of Hyd-PADRE:I9V:K:S9L

All the reagents were Peptide Synthesis Grade. Synthesis: Fmoc-Strategy, manual. Wang™ resin (substitution about 0.8 mmole/g). Fmoc-Leu-OH (>99%) was attached to the Wang™ resin (1 eq) by the symmetrical anhydride (5 eq)/DMAP (1 eq) method as described above using Fmoc-Val-OH and 1,3-DIC in a 2:1 ratio. The synthesis was started with 0.4 g Fmoc-Leu-Wang™ resin (approximately 0.22 mmole). The Fmoc group was deblocked at each step of the growing peptide chain by 20% piperidine/DMF treatment. All the amino acids used during chain elongation were Nα-Fmoc-protected, however amino acids with side chain functionalities were used with the additional protective groups: asparagine and histidine modified with trityl; lysine and tryptophan modified with Boc; glutamic acid, tyrosine, serine and threonine modified with t-butyl. Coupling of all amino acids was done using HBTU/DIEA reagents. After deprotection of the Fmoc group from the N-terminal alanine of the peptide chain assembled on the resin, HDA (1 eq) was introduced to the free amino group of alanine in the presence of DIC/HOBt reagent.

Final cleavage was achieved by treating the peptide-resin with TFA/thioanisole/EDT/water in a 90/5/2.5/2.5 ratio (2 hour treatment) at room temperature. This was followed by MTBE precipitation, filtration and drying of the product. Approximately 450 mg of crude product (about 30% purity, by analytical HPLC, method A) was obtained.

Purification of Hyd-Peptide

Purification was done on a Shimadzu™ HPLC system consisting of LC-8A binary pumps and a SPD-10A UV detector, using a VYDAC column (22×250 mm, packing material, C-4, 10µ, 300 A). Sample was prepared as follows. Approximately 450 mg crude peptide (purity about 40%) was purified in 2 lots. Each lot of about 220-230 mg peptide was dissolved in 40 mL 20% acetic acid/H$_2$O and filtered through a 0.45µ filter, then loaded on pre-equilibrated column through solenoid valve FCV-11AL (Shimadzu™) from port B, attached to the line of LC-8A Pump-A: flow rate=8 mL/minute; λ=220 nm; mobile phase=0.05% TFA, H$_2$O; mobile phase B=ACN. Mobile phases A and B were filtered through 0.2µ filter paper. The column was equilibrated with one column volume of mobile phase A (about 80 mL) and the sample was loaded as described above. One column volume of mobile phase A (about 80 mL) was run through the column, followed by the gradient below.

TABLE XIX

HPLC Mobile Phase

| Time (min.) | Gradient Conditions | |
|---|---|---|
| | % A | % B |
| 0.01 | 80 | 20 |
| 50 | 55 | 45 |
| 60 | 0 | 100 |
| 70 | 0 | 100 |
| 70.01 | 87 | 13 |
| 80 | Stop | |

The desired peak eluted between 25 and 40 minutes of the gradient run. The collected fractions were analyzed by analytical HPLC by Method A. All fractions containing pure peptide 85%) from all the four lots were pooled and concentrated on a Rotavapor™ to ⅓ of its original volume, then freeze-dried in a pre-weighed vial. About 70 mg of peptide was obtained. This freeze-dried material was analyzed by analytical HPLC (methods A (≥85% pure) and B (≥85% pure) as described above) and mass analysis using a Shimadzu-Kratos™ MALDI-TOF™ Kompact Probe™ mass analyzer. The calculated mass was 3553 a.m.u. and the experimental mass was 3553.3 a.m.u., which is within the stated error of the instrument.

Oligo 3

CpG-DNA fully phosphorothioated with 5'-end modified to aldehyde was obtained from Trilink Technologies™, analyzed by analytical HPLC as per Method B above and found to be about 60% pure.

Synthesis of Conjugate 6

All the reagents were DNA synthesis grade. Hyd-PADRE:I9V:K:S9L (SEQ ID NO:3) (5.8 mg, about 1.6 eq) was dissolved in 2 M urea solution (6 mL). Oligo 3 (13.4 mg, about 2.0 eq) was dissolved in 2 M urea (14 mL). The two solutions were mixed together and stirred for 3 hours at room temperature. The reaction mixture was filtered through a 0.45µ filter and passed through the preparative HPLC diphenyl column (10×250 mm) for desalting and purification: flow rate=4 mL/min; λ=260 nm; mobile phase A=10% ACN, 0.1 M TEAA, pH 5.0-5.1; mobile phase B=ACN. Mobile phases A and B were filtered through 0.2µ filter paper. The column was equilibrated with one column volume (about 20 mL) mobile phase A, and the sample loaded. One column volume (about 20 mL) was run through the column for desalting step, followed by the gradient below.

TABLE XX

HPLC Mobile Phase

| Time (min.) | Gradient Conditions | |
|---|---|---|
| | % A | % B |
| 0.01 | 100 | 0 |
| 40 | 40 | 60 |
| 45 | 0 | 100 |
| 60 | Stop | |

Figure 11:
FIG. 11 is a polyacrylamide gel. Lane 1=Oligo 3; lane 2-Conjugate 6; lane 3=Conjugate 5.

The desired peak eluted between 20-32 minutes of the gradient run. The peak collected above was concentrated on a Rotavapor™ to ⅓ of its original volume and then freeze dried in a pre-weighed vial. About 7.0 mg Conjugate 6 was obtained. This product was analyzed by HPLC (about 70-80% pure by method B above) and by PAGE (Method C), where it ran as a single band. See FIG. 11.

Example 6

Recognition of Naturally Processed HIV Epitopes

Figure 12:
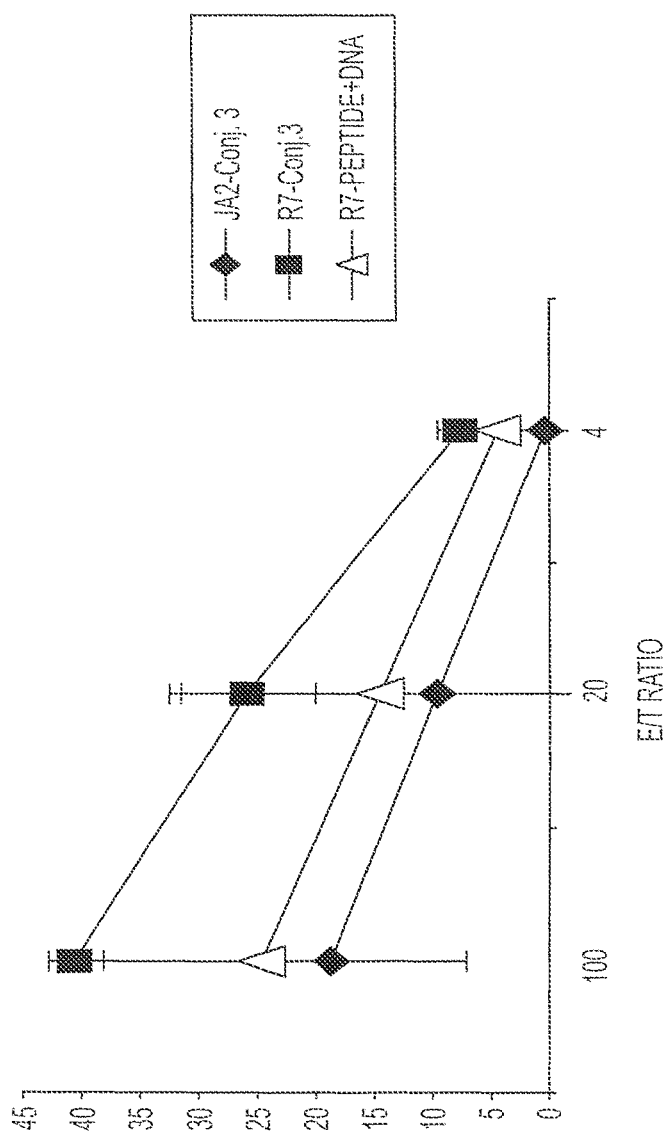
FIG. 12 shows percent lysis of human HIV-infected CD4$^+$ T cells (diamonds, JA2; triangles and squares, R7). P (T≤t) two-tail 0.03.

Splenic immune cells from mice immunized with Conjugate 3 (1 nmole) were subjected to one round of in vitro stimulation and tested for the ability to lyse HIV-infected CD4$^+$ cells (R7 cells). R7 cells are capable of synthesizing HIV particles that express p24, a characteristic diagnostic protein. The cells were tested at E:T ratios of 4, 20 and 100. Results are shown in FIG. 12, which also shows results for control JA2 cells. P (T<=t)=0.03 using a two-tail T test. The epitope recognized after immunization with Conjugate 3 is only a small portion of the total amount of peptides presented on the surface of the cells. This assay demonstrates recognition in one of the best in vitro systems to demonstrate that the immunization leads to recognition of bond fide HIV-infected cells. These results therefore indicate that the inventive approach to immunization is suitable for use in a clinical situation in which individuals are infected with HIV, for example for therapeutic use, or for prophylaxis against HIV.

Example 7

Figure 13:
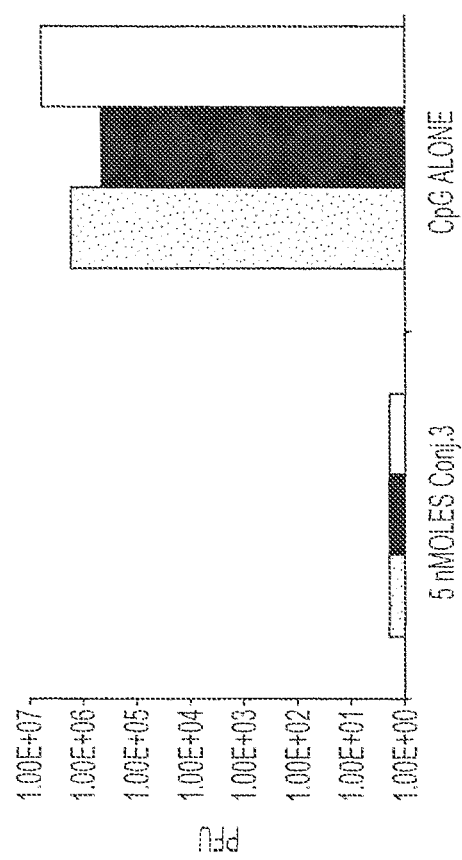
FIG. 13 shows response to challenge by surrogate virus after a single immunization with 5 nmoles Conjugate 3 versus CpG alone. Each bar provides data from a single mouse. Each treatment was performed on three mice.

Immunization Protects In Vivo Against Challenge with Vaccinia Virus Expressing the H1V-pol Gene Three mice were immunized with 5 nmole Conjugate 3 or CpG Sequence #1826 (control). Fourteen days after immunization, the mice were challenged by intraperitoneal administration of 1×10$^7$ p.f.u. of recombinant vaccinia virus expressing the HIV-pol gene. After five days, the virus titer in the ovaries of the mice was determined. Results are shown in FIG. 13. There was an approximate six orders of magnitude difference in protection in the case of mice immunized with Conjugate 3 versus control.

Figure 14:
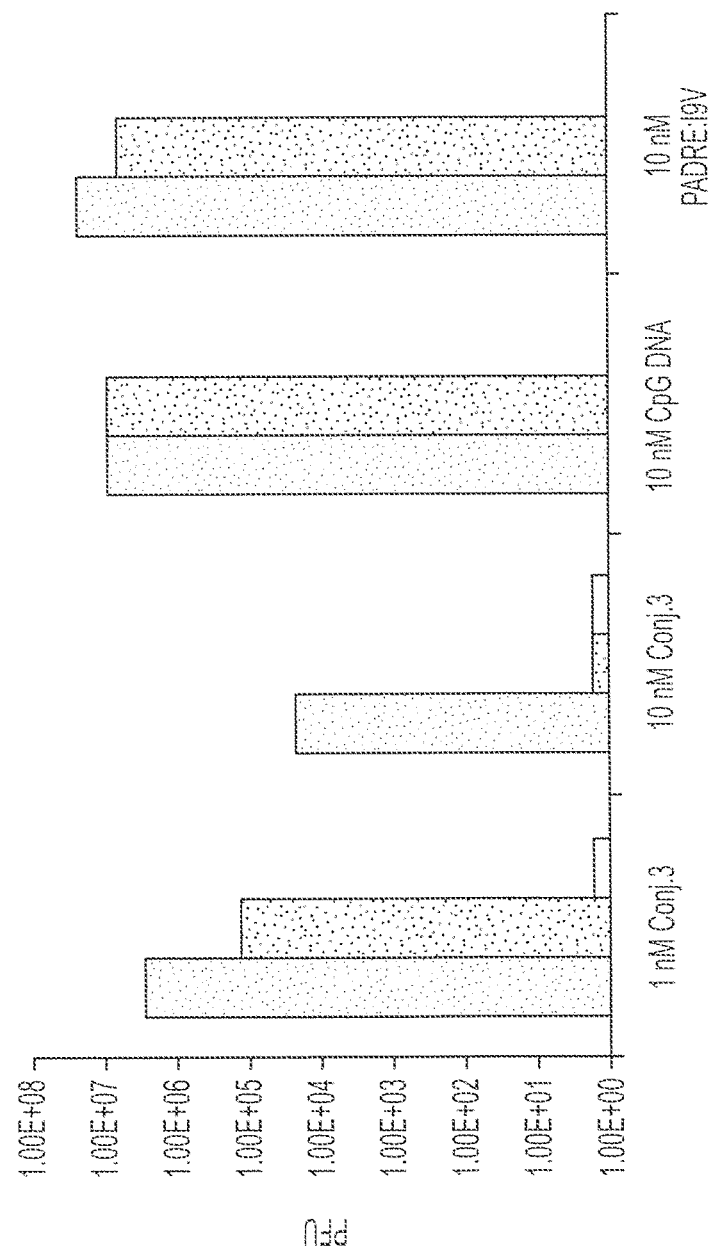
FIG. 14 shows response to challenge by recombinant vaccinia virus expressing the HIV-pol gene after a single intranasal administration of 1 or 10 nmole Conjugate 3 versus 10 nmole CpG DNA or PADRE:I9V peptide alone. (P≤0.02, Wilcoxon Two Sample Test). Each bar represents data from a single mouse. Each treatment was performed on two or three mice as shown.

This study was repeated using intranasal immunization. See FIG. 14. These HLA A2/Kb mice were immunized with 1 nmole Conjugate 3, 10 nmole PADRE:I9V or 10 nmole CpG DNA. Fourteen days after immunization, all mice were challenged intranasally with 2×10$^7$ p.f.u. recombinant vaccinia virus expressing HIV-pol. After five days, the virus titer in the mice ovaries was determined. The animals that were administered 10 nmoles of Conjugate 3 were significantly better at providing protection against the vaccinia virus challenge than animals immunized with the PADRE:

I9V peptide or animals receiving only CpG DNA without peptide (P=0.02; Wilcoxon two sample test). The results therefore indicate that vaccination with Conjugate 3 protects against viral infection in vivo.

Example 8

Vaccination with Conjugate Versus Unconjugated Peptide

Figure 15:
FIG. 15 shows response to challenge by recombinant vaccinia virus expressing HIV-pol after subcutaneous and intraperitoneal immunization with 1 nmole Conjugate 3 or 1 nmole PADRE:I9V peptide plus CpG DNA. Each bar provides data from a single mouse. Each treatment was performed on three mice.

HLA A2/Kb mice were immunized both subcutaneously and intraperitoneally with 1 nmole of Conjugate 3 or 1 nmole of PADRE:I9V peptide plus CpG DNA (unconjugated). Fourteen days later, the mice were challenged intraperitoneally with $1 \times 10^7$ p.f.u. of recombinant vaccinia virus expressing HIV-pol. After five days, the virus titer in the ovaries of the challenged mice was determined. Using a two-tailed T test, the difference between these two vaccine strategies was significant at p<0.02. See FIG. 15. Immunization with one dose of 1 nmole of Conjugate 3 provided protection against challenge with vaccinia virus expressing HIV-pol, whereas immunization with 1 nmole of the peptide with unconjugated CpG DNA did not confer protection against viral challenge. Ten-fold higher doses of unconjugated peptide vaccine were required to reach the same level of protection when the vaccine was administered as a conjugate.

Figure 16:
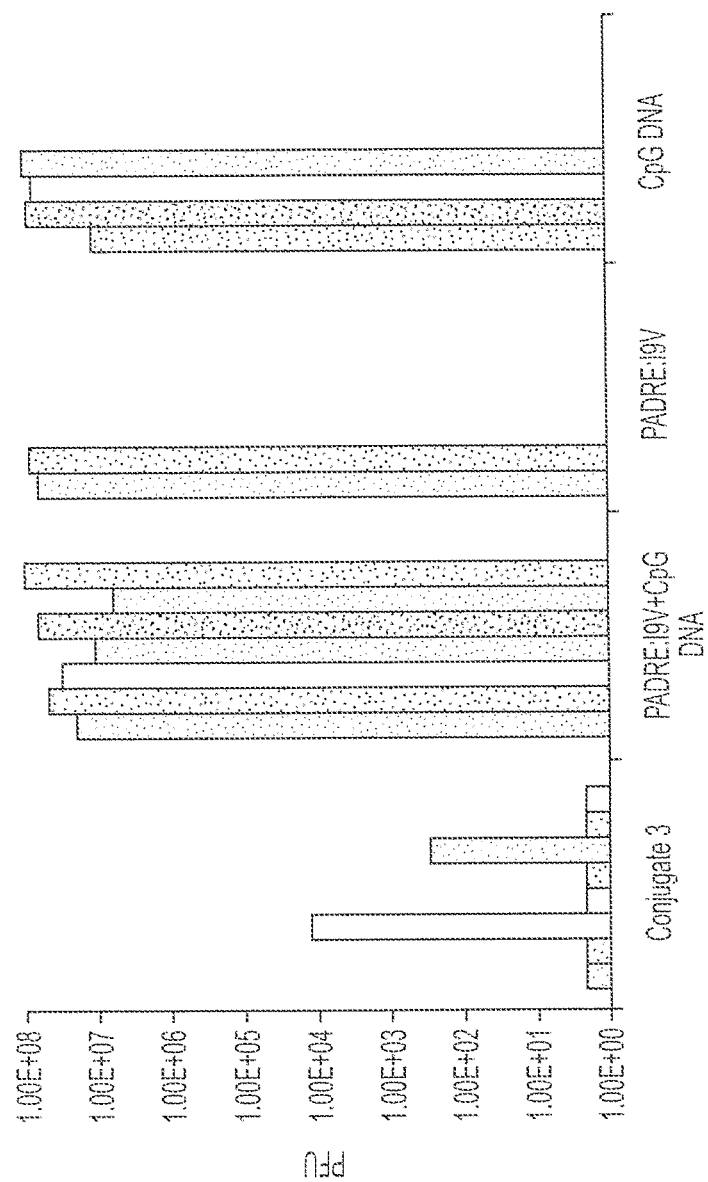
FIG. 16 shows response to challenge by recombinant vaccinia virus expressing HIV-pol after immunization with 0.1 nmole Conjugate 3 or peptide+DNA, fusion peptide or CpG DNA alone. Each bar provides data from a single mouse. Each treatment was performed on multiple mice as shown.

A lower dose of Conjugate 3 (0.1 nmole) was tested in comparison to a mixture of the peptide and CpG DNA. Two immunizations fourteen days apart were administered to mice, followed by challenge with $1 \times 10^7$ p.f.u. recombinant vaccinia virus expressing HIV-pol seven days after the second immunization. Five days later, the virus titer in the ovaries of the mice were determined. As is shown in FIG. 16, only the group vaccinated with Conjugate 3 received significant protection (P<0.02; Wilcoxon two sample test). Animals receiving either peptide, CpG DNA or both in combination were equivalently unprotected against viral challenge. Conjugate 3 was ten times more sensitive than peptide plus DNA (unconjugated) for protection against vaccinia virus infection.

Figure 17A:
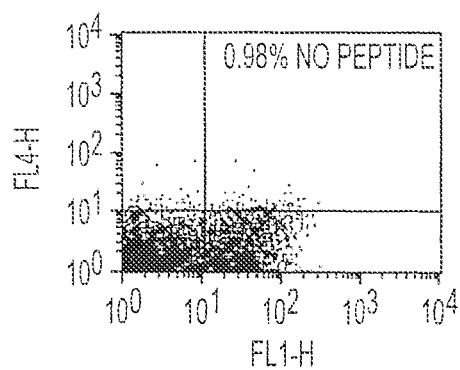
FIG. 17 is a set of three FACS results of cells stained to identify IFN-γ after immunization with Conjugate 4 (17C), peptide mix (17B) or DNA alone (17A).
Figure 17B:
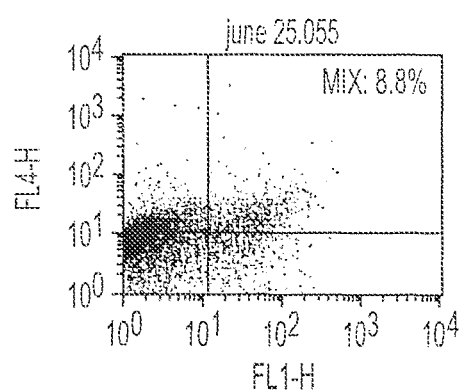
Figure 17C:
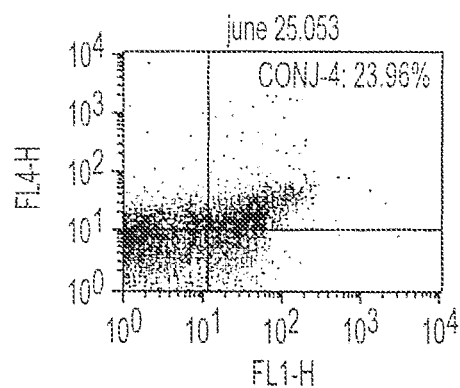

Conjugate 4, which is composed of CpG DNA #1826 (Oligo 3) linked using a HDA hydrazone linkage to PADRE followed by the HIV-gag CTL epitope SLYNTVATL (SEQ ID NO:6), was tested as described for Conjugate 3 above in comparison with unconjugated peptide. Chromium release assays and cytokine flow cytometry studies were carried out. One nanomole of the conjugate in a single immunization, followed by one in vitro stimulation, resulted in development of more than 23% HIV-gag CTL epitope-specific splenocytes (FIGS. 17B and 17A, respectively), greater than the mix of peptide plus DNA or DNA alone (FIG. 17C). This conjugate also caused cytotoxicity against peptide-sensitized targets and against the R7 cell line.

Methods for flow cytometry were as follows. Mice were immunized subcutaneously with either 1 nmole Conjugate 4 or 1 nmole KSS:PADRE:S9L (SEQ ID NO:2) and 1 nmole CpG DNA. One day 14, splenocytes from immunized mice were stimulated in vitro for 7 days with irradiated S9L-loaded LPS blasts from syngeneic litter mates. After the incubation, the cell mix was incubated further with S9L or irrelevant (control) peptide for six hours. The cells were passed through a Ficoll-Hypaque™ gradient, and the live cells were washed with phosphate buffered saline. One million cells were stained with CD8-FITC, then fixed and permeabilized by Perm/Fix™ solution for 30 minutes at 4° C. The cells then were washed in permeabilizing buffer and incubated with either anti-IFN-γ-APC or isotype-matched APC-labeled mAb. Two animals were analyzed for each vaccine and stimulation. See FIG. 17.

Example 9

HIV Immune Recognition after Multi-Epitope Peptide Vaccination

Conjugate 5 was synthesized to contain CpG DNA components in a linear chain with the CTL epitopes separated by a non-native asparagine residue (SEQ ID NOs:4 and 9). The conjugate was modified at the amino terminus as for Conjugates 3 and 4 and was physically evaluated by HPLC and gel electrophoresis. The conjugate was dissolved in saline solution and administered to HLA A2/Kb mice, and compared to a fusion peptide of all three CTL epitopes mixed with CpG DNA or to CpG DNA alone. Each vaccination contained 0.1 nmole vaccine component.

Figure 18:
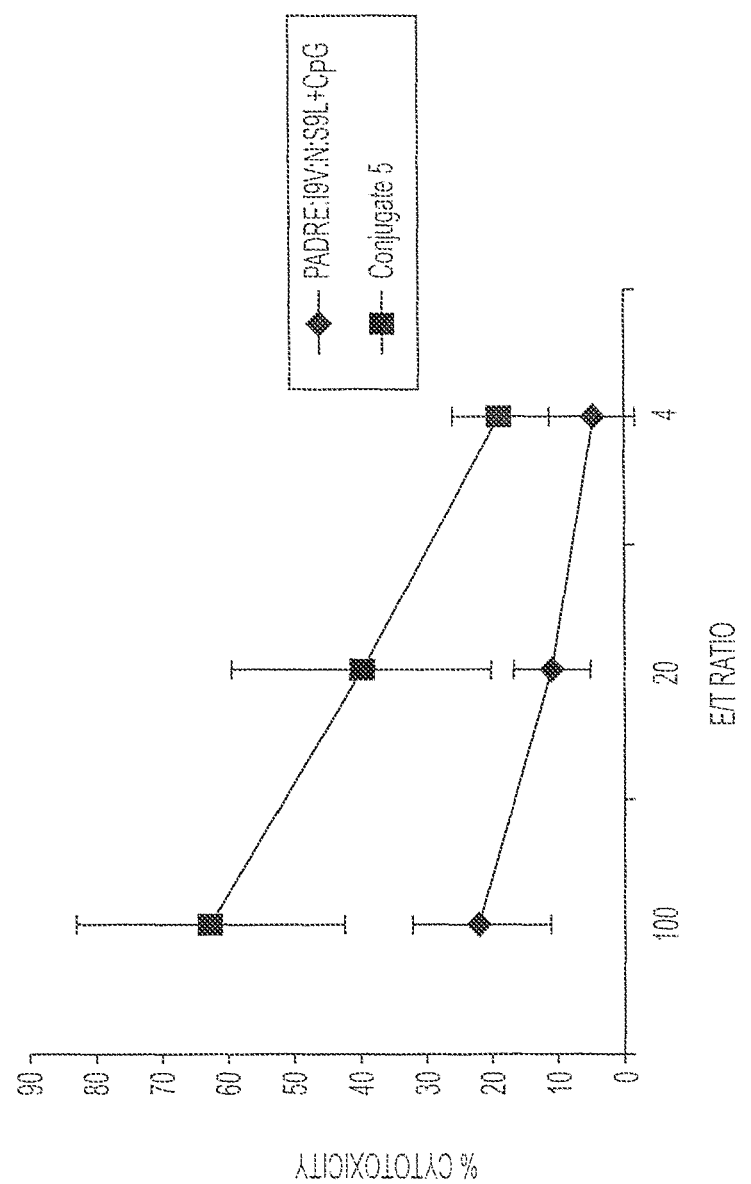
FIG. 18 shows percent cell lysis of targets by immune splenocytes after immunization with 0.1 nmole Conjugate 5 (Squares) or its individual components (diamonds). Targets were pre-loaded with I9V peptide (ILKEPVHGV; SEQ ID NO:5). P<0.03.
Figure 19:
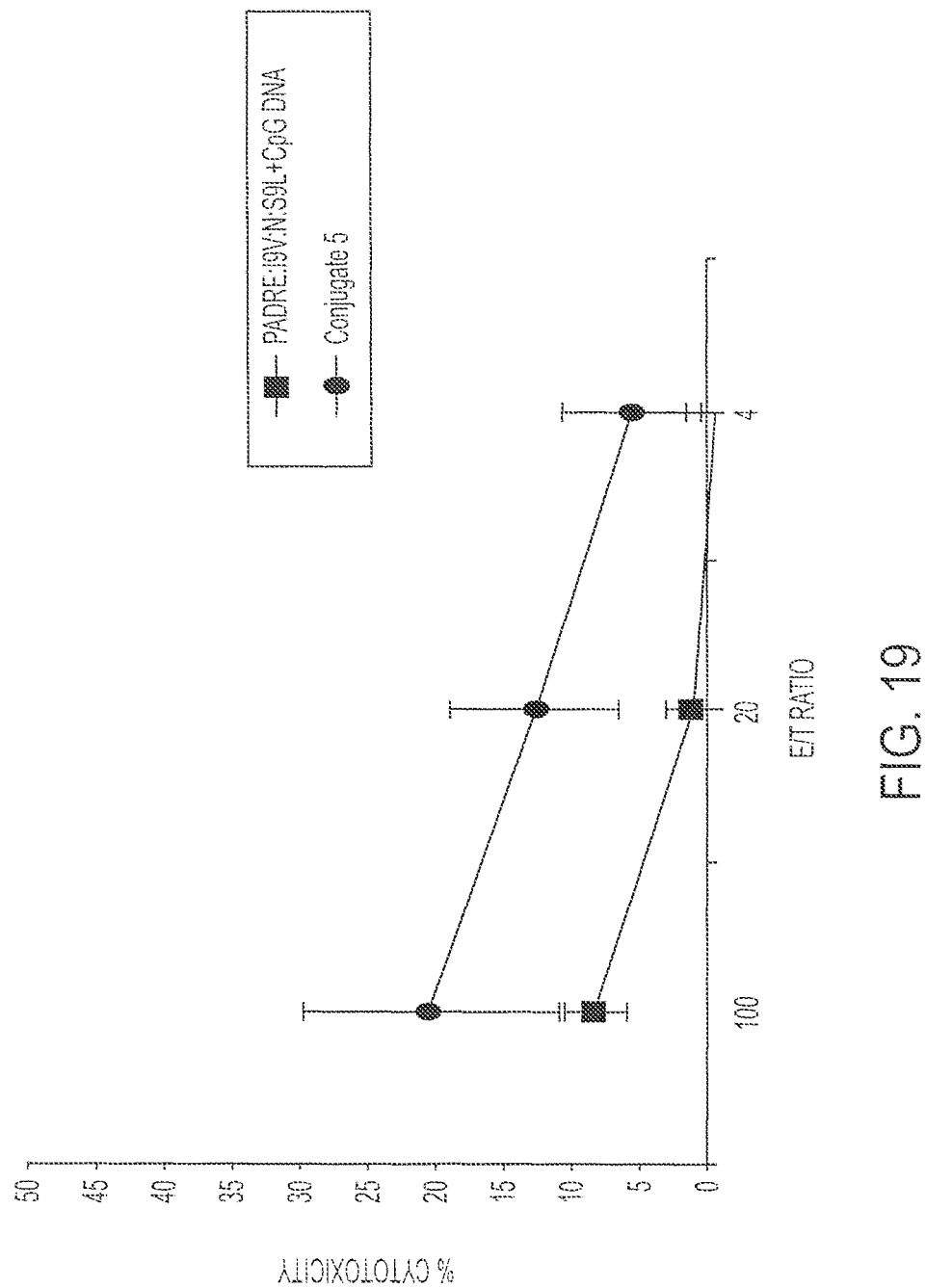
FIG. 19 shows percent cell lysis of targets by immunized splenocytes after immunization with 0.1 nmole Conjugate 5 (Circles) or its individual components (Squares). Targets were pre-loaded with S9L peptide (SLYNTVATL; SEQ ID NO:6). P<0.01.

Fourteen days after vaccination, splenocytes from individual mice were incubated with either I9V-loaded (FIG. 18) or S9L LPS blasts (FIG. 19 under in vitro stimulation conditions. Cytolytic T cell responses were determined by chromium release assay using either I9V-loaded targets (FIG. 18) or S9L-loaded targets (FIG. 19). The data in FIG. 18 shows a statistically significant (P<0.03) difference between the conjugated vaccine according to the invention and a mixture of the peptide and CpG DNA. Recognition of the S9L-loaded targets required a greater amount of conjugate in the immunization (10 nmoles). Nevertheless, a statistically significant (P<0.02) difference was found between the group immunized with Conjugate 5 versus the mixture of peptide plus DNA.

Figure 20:
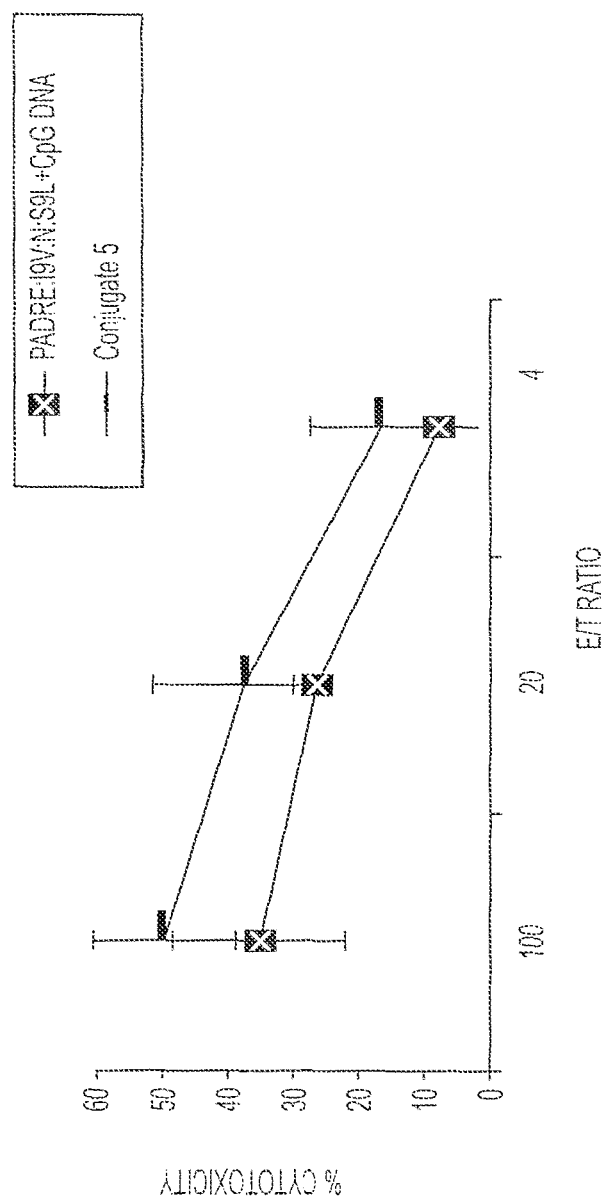
FIG. 20 shows cell lysis of R7 cells that were infected with HIV by splenocytes immunized with Conjugate 5 (Bars) or with its individual components (Squares). P<0.01.
Figure 21B:
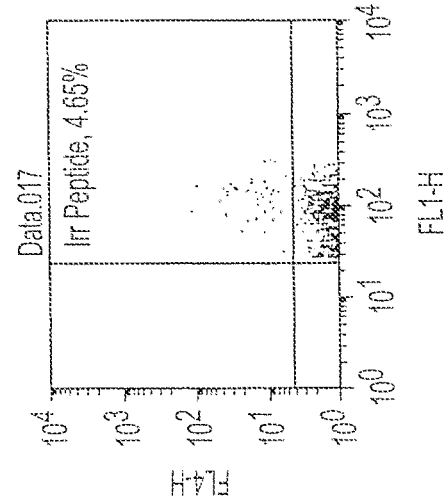
FIG. 21 provides histograms of the flow cytometry analysis of immune splenocytes for reaction with an isotype control (21A), an irrelevant, control peptide (21B), Conjugate 5 (21C) or fusion peptide plus DNA, unconjugated (21D).
Figure 21D:
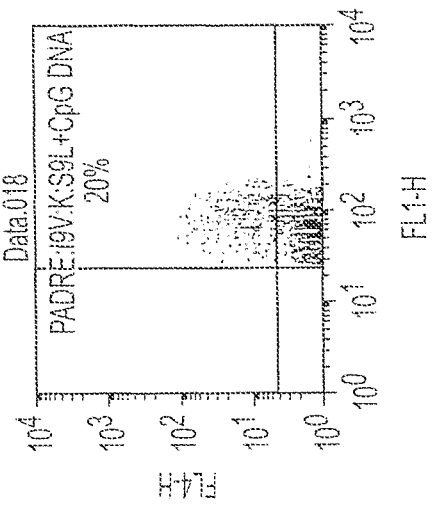
Figure 21A:
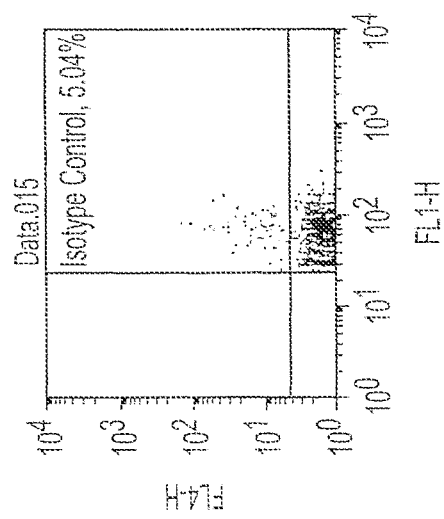
Figure 21C:
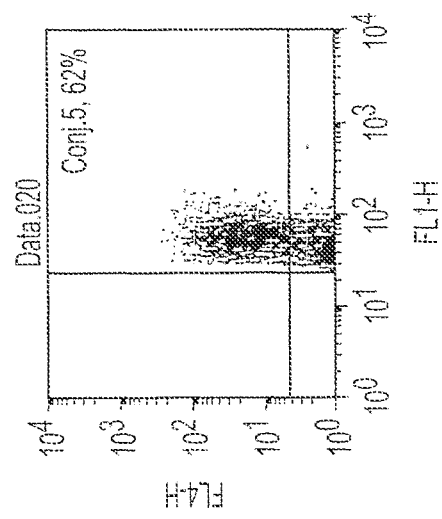

Additional targets were evaluated, including R7 cells that were infected with HIV. The level of recognition of the R7 target was higher with the multi-epitope peptide of Conjugate 5 than with Conjugate 3, even without conjugation. See FIG. 20. The comparison between the groups immunized with Conjugate 5 or a mixture of peptide plus DNA show that the difference in recognition of the R7 cells is significantly greater with Conjugate 5 (P<0.01). This demonstrates enhanced sensitivity of recognition of an HIV-infected cell line with Conjugate 5, and the level of recognition is much higher than with any of the conjugates containing one CTL epitope examined above.

The conjugate strategy can be extended to a greater number of epitopes or different epitopes that cover or apply to a wide variety of HIV strains and HLA types. Therefore, any single epitope or any combination of epitopes can be included in the peptide portion of the conjugate vaccines according to this invention. For example, two or more CTL epitopes may be included as a linear chain, with or without spacers between the epitopes, or three, four, five, six or more epitopes as desired to provide coverage for multi-ethnic populations, for different viral strains, or both.

Example 10

Flow Cytometry Analysis of Immune Splenocytes

Aliquots of the splenocytes evaluated above were evaluated by flow cytometry for expression of IFN-γ and for quantitation of the frequency of T cells specific for the relevant antigens. The immunization described in FIG. 18 was evaluated, with the modification that the splenocytes, instead of being incubated with cellular targets, were incubated with the I9V or irrelevant (control) peptide for six hours. The cells were passed through a Ficoll-Hypaque™ gradient and live cells were washed with phosphate-buffered saline. One million of the cells were stained with CD8-FITC. The cells then were fixed and permeabilized using Perm/Fix™ solution for 30 minutes at 4° C. Cells were washed in permeabilizing buffer and incubated with either anti-IFN-γ-allophycocyanin (APC) or isotype-matched APC-labeled mAb. See FIGS. 21A, 21B, 21C and 21D.

The data show that there was limited non-specific reaction of splenocytes to either an isotype control (FIG. 21A) or an irrelevant peptide (FIG. 21B), but that much more significant frequencies of reactive T cells were found after exposure to the I9V peptide in the case of immunization with the fusion peptide plus DNA, unconjugated (FIG. 20D), or with Conjugate 5 (FIG. 20C). The very high frequency of reactive T cells in FIG. 20C demonstrates a good correlation with the chromium release assay of FIGS. 17-19. The activity of Conjugate 5 is very high and affords a very high level of recognition by T cells, even after only one immunization. The extraordinary level of sensitivity in this well-recognized in vivo model for human cellular and humoral immune responses demonstrates the merit of this immunization approach.

Example 11

Effect of $T_H$ Epitope on Immunogenicity

Because the adjuvant activity of CpG was remarkable, experiments were performed to investigate the need for both CTL and $T_H$ epitope components in chimeric peptides for vaccine. Conjugate 7, which is CpG (oligo 3) covalently attached to the I9V peptide, was synthesized. See FIG. 3.

HHD II mice were immunized with 1 nmole of either Conjugate 7 or Conjugate 3 (which is the same as Conjugate 7 but also contains PADRE). A chromium release assay was performed using I9V-loaded JA2 cells as targets. See FIG. 22 for results. Conjugate 7 had less activity than Conjugate 3 against these cells (p<0.005).

Figure 22:
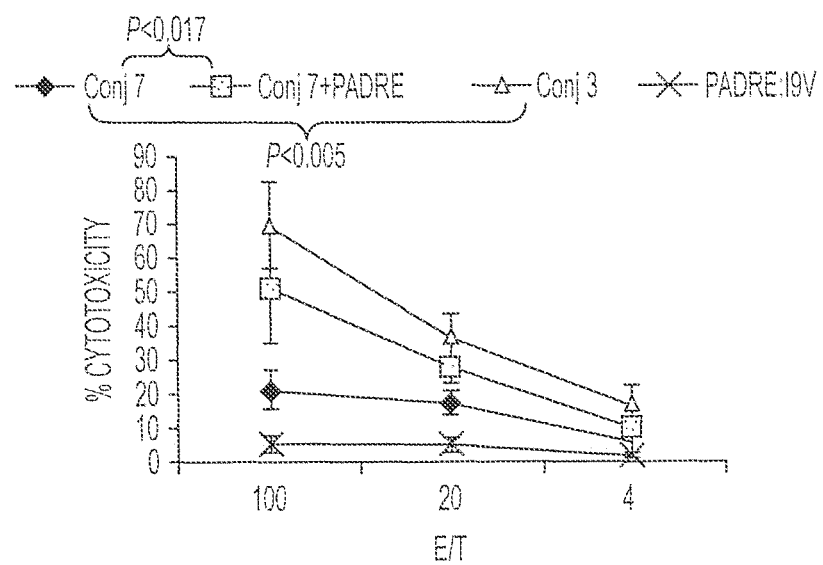
FIG. 22 shows results of a chromium release assay performed using I9V-loaded JA2 cells as targets and cells from HHD II mice immunized with either Conjugate 7 or Conjugate 3.

To address whether the defect in Conjugate 7 immunogenicity was the missing PADRE $T_H$ epitope, immunizations with Conjugate 7 plus PADRE $T_H$ were compared to immunizations with Conjugate 7 alone. Each of three mice were immunized with Conjugate 7 alone, Conjugate 7 together with the PADRE $T_H$ epitope, Conjugate 3, or the PADRE: I9V fusion peptide alone. FIG. 22 shows that the fusion peptide alone had little immunogenicity, while Conjugate 3 worked efficiently. Although Conjugate 7 had minimal immunogenicity when used alone, in combination with the free PADRE $T_H$ epitope, its immunogenicity was restored almost to the level of Conjugate 3. See FIG. 22. This demonstrates that both the $T_H$ and CTL epitopes should be present for maximal immunogenicity. Further, the majority of the stimulating activity of the PADRE epitope is caused by the sequence itself, rather than the artificial junction caused by chimerizing the CTL and $T_H$ epitopes, since Conjugate 3 and Conjugate 7 plus PADRE in trans have similar immunogenicity. Similar fusion peptides, including a fusion peptide composed of PADRE and an HPV-specific CTL epitope, have been administered to volunteers and women with cervical neoplasia without causing observable autoimmunity Example 12

Human-specific ODN

Figure 23:
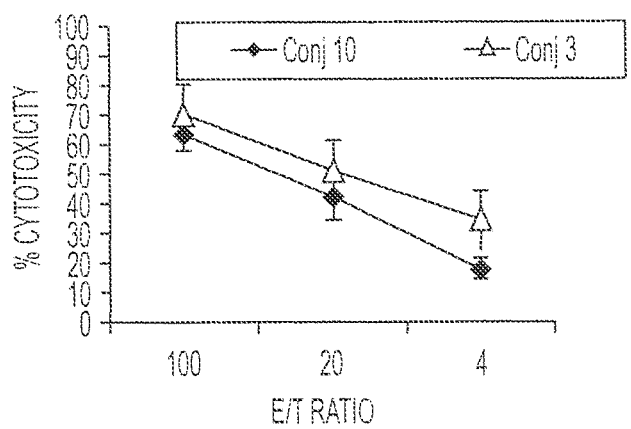
FIG. 23 presents percent cytotoxicity data for cells from HLA A2/Kb mice immunized with either Conjugate 3 or Conjugate 10.

Conjugate 10, composed of PADRE fused to I9V (SEQ ID NO:1), is identical to Conjugate 3 except for the substitution of the CpG portion, which is a primate- and human-specific CpG-ODN (Oligo 4; SEQ ID NO:10). See Hartmann et al., J. Immunol. 164:1617-1624, 2000. The chemical yield and purity of this conjugate were similar to the others synthesized above using CpG 1826 (murine). Groups of three HLA A2/Kb mice were immunized with either Conjugate 3 and Conjugate 10 (1 nmole). Chromium release assay results in FIG. 23 show that both conjugates were recognized equivalently, providing additional evidence that these constructs are feasible for use in a clinical setting in human patients. The CpG-ODN used in Conjugate 10 also is known under the trade names ProMune™ or Vaxmune™ (Coley Pharmaceutical Group).

TABLE XXI

Summary of Conjugate Structures and Sequences

| NAME | SEQ ID NO | SEQUENCE OR STRUCTURE |
| --- | --- | --- |
| PADRE:I9V | 1 | AKXVAAWTLKAAAILKEPVHGV, X = cyclohexylalanine |
| KSS:PADRE:S9L | 2 | KSSAKXVAAWTLKAAASLYNTVATL, X = cyclohexylalanine |
| PADRE:I9V:K:S9L | 3 | AKXVAAWTLKAAAILKEPVHGVKSLYNTVATL, X = cyclohexylalanine |
| PADRE:I9V:N:S9L | 4 | AKXVAAWTLKAAAILKEPVHGVNSLYNTVATL, X = cyclohexylalanine |
| I9V | 5 | ILKEPVHGV |
| S9L | 6 | SLYNTVATL |
| Oligo 1 | 7 | Phosphodiester single-stranded CpG DNA 5'-tccatgacgttcctgacgtt-3' with the 5' end modified to thiohexyl |
| Oligo 2 | 8 | Phosphorothioated backbone, single-stranded CpG DNA 5'-tccatgacgttcctgacgtt-3' with the 5' end modified to thiohexyl |
| Oligo 3 | 9 | Phosphorothioated backbone, single-stranded CpG DNA 5'-H-CO-$C_6H_3$-CO-NH-$(CH_2)_6$-tccatgacgttcctgacgtt-3' (5'-aldehyde linker: Amidite-A ™) |

TABLE XXI-continued

Summary of Conjugate Structures and Sequences

| NAME | SEQ ID NO | SEQUENCE OR STRUCTURE |
| --- | --- | --- |
| Oligo 4 | 10 | 5'-tcgtcgttttgtcgttttgtcgtt-3' (phosphorothioate-substituted) |
| Oligo 5 | 11 | 5'-ggGGGACGATCGTCgggggG-3' (phosphorothioate-substituted at lower case letters) |
| PADRE | 12 | AKXVAAWTLKAAA, X = cyclohexylalanine |
| Conjugate 1 | NA | PADRE-I9V + Oligo 1 |
| Conjugate 2 | NA | PADRE-I9V + Oligo 2 |
| Conjugate 3 | NA | PADRE:I9V + Oligo 3 |
| Conjugate 4 | NA | KSS:PADRE:S9L + Oligo 3 |
| Conjugate 5 | NA | PADRE:I9V:N:S9L + Oligo 3 |
| Conjugate 6 | NA | PADRE:I9V:K:S9L + Oligo 3 |
| Conjugate 7 | NA | AAA:I9V + Oligo 3 |
| Conjugate 10 | NA | PADRE:I9V + Oligo 4 |
| Hyd | NA | $NH_2$-NH-$C_6H_3$N-CO- |

REFERENCES

1. Cho et al., "IFN-alpha beta promote priming of antigen-specific CD8+ and CD4+ T lymphocytes by immunostimulatory DNA-based vaccines." *J. Immunol.* 168:4907-4913, 2002.
2. Cho et al., "Immunostimulatory DNA-based vaccines induce cytotoxic lymphocyte activity by a T-helper cell-independent mechanism." *Nat. Biotechnol.* 18:509-514, 2000.
3. Hartmann et al., "Delineation of a CpG phosphorothioate oligodeoxynucleotide for activation primate immune responses in vitro and in vivo." *J. Immunol.* 164:1617-1624, 2000.
4. Homer et al., "Immunostimulatory DNA-based vaccines elicit multifaceted immune responses against HIV at systemic and mucosal sites." *J. Immunol.* 167:1584-1591, 2001.
5. Livingston et al., "The Hepatitis B virus-specific CTL responses induced in humans by lipopeptide vaccination are comparable to those elicited by acute viral infection." *J. Immunol.* 159:1383-1392, 1997.
6. Schirmbeck et al., "Antigenic epitopes fused to cationic peptide bound to oligonucleotides facilitate toll-like receptor 9-dependent, but CD4+ T cell help-independent priming of CD8+ T cells." *J. Immunol.* 171:5198-5207, 2003.
7. Tighe et al., "Conjugation of protein to immunostimulatory DNA results in rapid, long-lasting and potent induction of cell-mediated and humoral immunity," *Eur. J. Immunol.* 30(7):1939-1947, 2000.
8. Tighe et al., "Conjugation of immunostimulatory DNA to the short ragweed allergen and a 1 enhances its immunogenicity and reduces its allergenicity." *J. Allergy Clin. Immunol.* 106(1 Pt. 1):124-134, 2000.
9. Vitiello et al., "Development of a lipopeptide-based therapeutic vaccine to treat chronic HBV infection. I. Induction of a primary cytotoxic T lymphocyte response in humans." *J. Clin. Invest.* 95:341-349, 1995.

The invention claimed is:

1. A method of increasing the effectiveness of an antigenic peptide CTL epitope vaccine component, the method comprises conjugating a fusion peptide to a DNA oligomer, wherein the fusion peptide comprises a T-help epitope and an antigenic peptide CTL epitope, wherein the antigenic peptide CTL epitope is conjugated to the DNA oligomer, and wherein the antigenic peptide CTL epitope is amino acid residues 14-32 of SEQ ID NO:3 or amino acid residues 14-32 of SEQ ID NO:4.

2. The method of claim 1, wherein the DNA oligomer comprises a CpG sequence.

3. The method of claim 2, wherein the DNA oligomer is a phosphodiester CpG DNA.

4. The method of claim 2, wherein the DNA oligomer is a fully phosphorothioated backbone CpG DNA.

5. The method of claim 1, wherein the DNA oligomer comprises about 8 to about 300 nucleotide bases.

6. The method of claim 5, wherein the DNA oligomer comprises about 15 to about 100 nucleotide bases.

7. The method of claim 5, wherein the DNA oligomer comprises about 20 to about 25 nucleotide bases.

8. The method of claim 1, wherein the fusion peptide is synthetic.

* * * * *

UNITED STATES PATENT AND TRADEMARK OFFICE
CERTIFICATE OF CORRECTION

PATENT NO. : 10,596,254 B2  
APPLICATION NO. : 15/963173  
DATED : March 24, 2020  
INVENTOR(S) : Don J. Diamond Page 1 of 1

It is certified that error appears in the above-identified patent and that said Letters Patent is hereby corrected as shown below:

In the Specification

Column 1, Lines 20-26:
"This invention was made with government support in the form of Grant No. AI44313 from the United States Department of Health and Human Services, National Institutes of Health, DAIDS and Grant No. PO1CA30206 from the United States Department of Health and Human Services, National Institutes of Health, NCI. The United States government has certain rights in the invention."

Should be:
-- This invention was made with government support under CA030206, and AI044313 awarded by the National Institutes of Health. The government has certain rights in the invention. --

Signed and Sealed this  
Twenty-fourth Day of October, 2023

Katherine Kelly Vidal  
*Director of the United States Patent and Trademark Office*